(12) United States Patent
Cornero et al.

(10) Patent No.: US 11,912,740 B2
(45) Date of Patent: Feb. 27, 2024

(54) HONEY PROTEOMICS FOR HONEYBEE DISEASE AND ENVIRONMENTAL BIOMONITORING

(71) Applicant: George Mason University, Fairfax, VA (US)

(72) Inventors: Rocio Solange Cornero, Arlington, VA (US); Alessandra Luchini Kunkel, Burke, VA (US); Lance A. Liotta, Fairfax, VA (US); Claudius Mueller, Warrenton, VA (US)

(73) Assignee: GEORGE MASON RESEARCH FOUNDATION, INC., Fairfax, VA (US)

( * ) Notice: Subject to any disclaimer, the term of this patent is extended or adjusted under 35 U.S.C. 154(b) by 628 days.

(21) Appl. No.: 17/115,988

(22) Filed: Dec. 9, 2020

(65) Prior Publication Data
US 2021/0198308 A1    Jul. 1, 2021

Related U.S. Application Data

(60) Provisional application No. 62/955,618, filed on Dec. 31, 2019.

(51) Int. Cl.
| | | |
|---|---|---|
| *C07K 1/22* | (2006.01) | |
| *G01N 33/58* | (2006.01) | |
| *G01N 33/68* | (2006.01) | |
| *B01J 20/28* | (2006.01) | |
| *B01J 20/26* | (2006.01) | |
| *B01J 20/285* | (2006.01) | |

(52) U.S. Cl.
CPC ............... *C07K 1/22* (2013.01); *B01J 20/261* (2013.01); *B01J 20/262* (2013.01); *B01J 20/285* (2013.01); *B01J 20/28016* (2013.01); *B01J 20/28023* (2013.01); *G01N 33/587* (2013.01); *G01N 33/6848* (2013.01); *G01N 2800/50* (2013.01)

(58) Field of Classification Search
None
See application file for complete search history.

(56) References Cited

U.S. PATENT DOCUMENTS

2009/0148961 A1    6/2009 Luchini et al.

OTHER PUBLICATIONS

Tamburro et al., "Multifunctional Core-Shell Nanoparticles: Discovery of Previously Invisible Biomarkers", J. Am. Chem. Soc. 2011, 133, 19178-19188.

*Primary Examiner* — Xiaoyun R Xu
(74) *Attorney, Agent, or Firm* — WC&F IP

(57) ABSTRACT

Methods for isolating proteins from a honey sample are provided. The methods include contacting the honey sample with a substrate functionalized with one or more reactive dyes and recovering proteins associated with the substrate. Methods for detecting proteins in a honey sample and assessing the risk of colony collapse disorder are also provided.

5 Claims, 10 Drawing Sheets
Specification includes a Sequence Listing.

SEQUENCE LISTING

<160> NUMBER OF SEQ ID NOS: 41

<210> SEQ ID NO 1

```
<211> LENGTH: 98
<212> TYPE: PRT
<213> ORGANISM: Apis mellifera

<400> SEQUENCE: 1

Pro Asn Asp Ala Gln Pro Tyr Ile Phe Gln Glu Val Ile Asp Tyr Gly
1               5                   10                  15

Asn Glu Ala Ile Ser Lys Arg Gly Thr Lys Ile Asp Asn Trp Trp Asp
            20                  25                  30

Asn Gly Ser Asn Gln Ile Ala Phe Ser Arg Asn Thr Ala Tyr Asn Phe
        35                  40                  45

Asp Tyr Pro Gln Val Pro Tyr Thr Val Lys Ala Asn Thr Tyr Asn Phe
50                  55                  60

Asp Tyr Pro Gln Val Pro Tyr Thr Val Lys Asn Phe His Pro Arg Glu
65                  70                  75                  80

Gln Phe Ile Asp Met Val Ala Arg Tyr Ser Tyr Glu Ile Ser Asn Ala
                85                  90                  95

Phe Arg

<210> SEQ ID NO 2
<211> LENGTH: 129
<212> TYPE: PRT
<213> ORGANISM: Apis mellifera

<400> SEQUENCE: 2

Tyr Leu His Gln Phe Ala Pro Glu Gln Pro Asp Leu Asn Tyr Tyr Asn
1               5                   10                  15

Pro Val Val Leu Asp Asp Met Gln Asn Val Leu Arg Leu His Gln Phe
            20                  25                  30

Ala Pro Glu Gln Pro Asp Leu Asn Tyr Tyr Asn Pro Val Val Leu Asp
        35                  40                  45

Asp Met Gln Asn Val Leu Arg Ile Leu Ile Ser Gln Asp Ala Lys Phe
50                  55                  60

Gly Asn Phe Gln Ala Tyr Tyr Leu His Gln Phe Ala Pro Glu Gln Pro
65                  70                  75                  80

Asp Leu Asn Tyr Tyr Asn Pro Val Val Leu Asp Asp Met Gln Asn Val
                85                  90                  95

Leu Arg Asp Val Leu Asp Glu Phe Pro Gln Pro Lys Phe Leu Asp Glu
            100                 105                 110

Pro Leu Ser Gly Glu Thr Asn Asp Pro Asn Lys Thr Glu Tyr Thr Leu
        115                 120                 125

Lys

<210> SEQ ID NO 3
<211> LENGTH: 127
<212> TYPE: PRT
<213> ORGANISM: Apis mellifera

<400> SEQUENCE: 3

Leu Thr Leu Asp Asn Asn Gln Ser Val Gln Val Arg Ile Thr Leu Asp
1               5                   10                  15

Asn Asn Gln Ser Val Gln Val Arg Ser Gln Leu Asp Asp Ile Tyr Asp
            20                  25                  30

Tyr Leu Glu Phe Asn Ala Gly Pro Leu Arg Ser Asn Lys Glu Phe Asp
        35                  40                  45

Phe Val Ile Ile Gly Gly Gly Thr Ala Gly Ser Ile Leu Ala Arg Val
50                  55                  60
```

```
Ile Asp Ala Ser Ile Met Pro Glu Val Thr Ser Gly Asn Thr Asn Ala
 65                  70                  75                  80

Pro Thr Met Met Ile Ala Glu Lys Gly Ala Asp Ile Ile Lys Gln Asp
                 85                  90                  95

Trp Gly Val Lys Val Asn Asp Val Leu Arg Ser Asn Lys Glu Phe Asp
            100                 105                 110

Phe Val Ile Ile Gly Gly Gly Thr Ala Gly Ser Ile Leu Ala Arg
        115                 120                 125

<210> SEQ ID NO 4
<211> LENGTH: 12
<212> TYPE: PRT
<213> ORGANISM: gamma proteobacterium N4-7

<400> SEQUENCE: 4

Leu Val Met Glu Leu Tyr Ala Asp Asn Val Asn Lys
1               5                   10

<210> SEQ ID NO 5
<211> LENGTH: 18
<212> TYPE: PRT
<213> ORGANISM: Pseudomonas sp. 101

<400> SEQUENCE: 5

Asp Ser Ala Pro Ala Val Val Thr Ile Glu Gly Ala Ser Asp Ala Asp
1               5                   10                  15

Gly Lys

<210> SEQ ID NO 6
<211> LENGTH: 19
<212> TYPE: PRT
<213> ORGANISM: Snodgrassella alvi

<400> SEQUENCE: 6

Gln Leu Tyr Asp Thr Asn Asn Asp Val Ser Asn Leu Ser Ser Ser Leu
1               5                   10                  15

Thr Thr Lys

<210> SEQ ID NO 7
<211> LENGTH: 16
<212> TYPE: PRT
<213> ORGANISM: Lactobacillus sp. 30A

<400> SEQUENCE: 7

Glu Gly Gly His Thr Val Gly Ala Gly Val Val Ser Asp Ile Glu Glu
1               5                   10                  15

<210> SEQ ID NO 8
<211> LENGTH: 8
<212> TYPE: PRT
<213> ORGANISM: Microbacterium sp.

<400> SEQUENCE: 8

Gln Met Met Gly Asp Thr Leu Arg
1               5

<210> SEQ ID NO 9
<211> LENGTH: 12
<212> TYPE: PRT
<213> ORGANISM: Bifidobacterium sp.

<400> SEQUENCE: 9
```

```
Gly Ala Val Glu Ser Pro Gly Ala Val Ala Tyr Pro
1               5                   10

<210> SEQ ID NO 10
<211> LENGTH: 8
<212> TYPE: PRT
<213> ORGANISM: Gilliamella sp.

<400> SEQUENCE: 10

Asp Asp Tyr Pro Asp Gly Pro Lys
1               5

<210> SEQ ID NO 11
<211> LENGTH: 17
<212> TYPE: PRT
<213> ORGANISM: Varroa destructor

<400> SEQUENCE: 11

Val Asn Gly Gly Gly Gly Ala Leu Gly Gly Gly Gly Ser Gly Met Leu
1               5                   10                  15

Lys

<210> SEQ ID NO 12
<211> LENGTH: 8
<212> TYPE: PRT
<213> ORGANISM: Paenibacillus apiarius

<400> SEQUENCE: 12

Phe Gln Leu Gln Asp Pro Leu Arg
1               5

<210> SEQ ID NO 13
<211> LENGTH: 15
<212> TYPE: PRT
<213> ORGANISM: Ascosphaera apis

<400> SEQUENCE: 13

Asp Val Met Arg Ala Gly Ser His Met Gly Leu Gly Gln Phe Arg
1               5                   10                  15

<210> SEQ ID NO 14
<211> LENGTH: 16
<212> TYPE: PRT
<213> ORGANISM: Aspergillus sparsus

<400> SEQUENCE: 14

Ser Ala Ala Gly Asn Val Ile Asp Ser Gly Ala Thr Thr Pro Thr Lys
1               5                   10                  15

<210> SEQ ID NO 15
<211> LENGTH: 8
<212> TYPE: PRT
<213> ORGANISM: Nosema ceranae

<400> SEQUENCE: 15

Lys Lys Gln Asp His Asn Leu Arg
1               5

<210> SEQ ID NO 16
<211> LENGTH: 11
<212> TYPE: PRT
<213> ORGANISM: Tropilaelaps mercedesae

<400> SEQUENCE: 16
```

```
Leu Met Asn Asp Asp Val Phe Ala Ala Tyr Arg
1               5                   10

<210> SEQ ID NO 17
<211> LENGTH: 18
<212> TYPE: PRT
<213> ORGANISM: Apis mellifera filamentous virus

<400> SEQUENCE: 17

Val Thr Thr Ala Pro Leu Arg Ala Gln Ala Ser Ser Pro Thr Gln Ser
1               5                   10                  15

Gly Arg

<210> SEQ ID NO 18
<211> LENGTH: 35
<212> TYPE: PRT
<213> ORGANISM: Arabidopsis thaliana

<400> SEQUENCE: 18

Trp Gly Gly Gly Met Gly Gly Gly Gly Gly Gly Gly Gly Gly Ser Gly
1               5                   10                  15

Gly Gly Gly Gly Gly Arg Gly Gly Gly Pro Pro Arg Gly Gly Leu Asp
            20                  25                  30

Asn Val Arg
        35

<210> SEQ ID NO 19
<211> LENGTH: 13
<212> TYPE: PRT
<213> ORGANISM: Brassica sp.

<400> SEQUENCE: 19

Leu Tyr Phe Tyr Gln Asp Thr Gly Pro Thr Pro Ala Arg
1               5                   10

<210> SEQ ID NO 20
<211> LENGTH: 12
<212> TYPE: PRT
<213> ORGANISM: Cinnamomum micranthum f. kanehirae

<400> SEQUENCE: 20

Val Met Ser Asn Glu Glu Ala Val Asn Ser Leu Arg
1               5                   10

<210> SEQ ID NO 21
<211> LENGTH: 11
<212> TYPE: PRT
<213> ORGANISM: Nymphaea colorata

<400> SEQUENCE: 21

Leu Leu Gly Ala Asn Val Asn Asn Leu Leu Lys
1               5                   10

<210> SEQ ID NO 22
<211> LENGTH: 14
<212> TYPE: PRT
<213> ORGANISM: Papaver somniferum

<400> SEQUENCE: 22

Leu Leu Glu Glu Phe Gly Tyr Gln Glu Val Gly His Leu Arg
1               5                   10
```

-continued

```
<210> SEQ ID NO 23
<211> LENGTH: 12
<212> TYPE: PRT
<213> ORGANISM: Parasponia andersonii

<400> SEQUENCE: 23

Leu Leu Met Glu Leu Tyr Ala Asp Val Val Pro Arg
1               5                   10

<210> SEQ ID NO 24
<211> LENGTH: 13
<212> TYPE: PRT
<213> ORGANISM: Prunus sp.

<400> SEQUENCE: 24

Phe Ala Thr Thr Ser Ala His Asp Phe Ser Tyr Met Lys
1               5                   10

<210> SEQ ID NO 25
<211> LENGTH: 13
<212> TYPE: PRT
<213> ORGANISM: Pyrus sp.

<400> SEQUENCE: 25

Gly Val Asn Pro Asn Asn Ala Ala Thr Leu Pro Ala Lys
1               5                   10

<210> SEQ ID NO 26
<211> LENGTH: 15
<212> TYPE: PRT
<213> ORGANISM: Rosa chinensis

<400> SEQUENCE: 26

Thr Thr Gly Asp Leu Gly Asp Asn Trp Asn Ser Met Thr Ser Arg
1               5                   10                  15

<210> SEQ ID NO 27
<211> LENGTH: 11
<212> TYPE: PRT
<213> ORGANISM: Saccharum sp. H32-8560

<400> SEQUENCE: 27

Arg Pro Ser Ser Leu Val Gly Glu Glu Leu Lys
1               5                   10

<210> SEQ ID NO 28
<211> LENGTH: 14
<212> TYPE: PRT
<213> ORGANISM: Solanum spegazzinii

<400> SEQUENCE: 28

Glu Thr Val Ser Gly Glu Met Ile Leu Asn Val Lys Ser Lys
1               5                   10

<210> SEQ ID NO 29
<211> LENGTH: 14
<212> TYPE: PRT
<213> ORGANISM: Vitis vinifera

<400> SEQUENCE: 29

Ser Leu Ala Ser Asp Ala Ser Ala Ala Ala Thr Trp Val Arg
1               5                   10

<210> SEQ ID NO 30
<211> LENGTH: 26
```

<212> TYPE: PRT
<213> ORGANISM: Aureobasidium pullulans

<400> SEQUENCE: 30

Pro Ser Thr Ser His Ser Asn Val Thr Ala Ala Asn Asp Asp Met Ser
1               5                   10                  15

Glu Lys Gln Ala Ile Glu Gly Gly Pro Arg
            20                  25

<210> SEQ ID NO 31
<211> LENGTH: 8
<212> TYPE: PRT
<213> ORGANISM: Blumeria graminis

<400> SEQUENCE: 31

Arg Glu Arg Asp Gln Ser Met Arg
1               5

<210> SEQ ID NO 32
<211> LENGTH: 11
<212> TYPE: PRT
<213> ORGANISM: Burkholderia sp. arc1

<400> SEQUENCE: 32

Glu Pro Ala Ala Asn Pro Asp Thr Thr Ala Arg
1               5                   10

<210> SEQ ID NO 33
<211> LENGTH: 11
<212> TYPE: PRT
<213> ORGANISM: Diaporthe helianthin

<400> SEQUENCE: 33

Phe Phe Thr Val Asn Gly Pro Asn Ser Pro Arg
1               5                   10

<210> SEQ ID NO 34
<211> LENGTH: 8
<212> TYPE: PRT
<213> ORGANISM: Erwinia sp.

<400> SEQUENCE: 34

Phe Trp Gln Val Leu Ser Pro Arg
1               5

<210> SEQ ID NO 35
<211> LENGTH: 11
<212> TYPE: PRT
<213> ORGANISM: Monilinia fructicola

<400> SEQUENCE: 35

Asn Leu Ala Pro Lys Cys Asp Glu Val Tyr Arg
1               5                   10

<210> SEQ ID NO 36
<211> LENGTH: 12
<212> TYPE: PRT
<213> ORGANISM: Monosporascus cannonballus

<400> SEQUENCE: 36

Thr Met Tyr Ser Ser Leu Asn Pro Thr Thr Asn Lys
1               5                   10

<210> SEQ ID NO 37

```
<211> LENGTH: 18
<212> TYPE: PRT
<213> ORGANISM: Pantoea sp.

<400> SEQUENCE: 37

Ser Pro Ser Ala Glu Val Ala Lys Met Val Glu Asp Asp Leu Gly Asn
1               5                   10                  15

Gln Arg

<210> SEQ ID NO 38
<211> LENGTH: 11
<212> TYPE: PRT
<213> ORGANISM: Pectobacterium sp.

<400> SEQUENCE: 38

Asn Ala Val Asn Asp Leu Leu Met Ser Gln Arg
1               5                   10

<210> SEQ ID NO 39
<211> LENGTH: 9
<212> TYPE: PRT
<213> ORGANISM: Pseudomonas syringae

<400> SEQUENCE: 39

Ser Gly Asn Gln Ile Ala Phe Ser Arg
1               5

<210> SEQ ID NO 40
<211> LENGTH: 21
<212> TYPE: PRT
<213> ORGANISM: Rhodotorula toruloides

<400> SEQUENCE: 40

Cys Leu Phe Gly Glu Ala Asp Glu Ala Gly Glu Leu Asp Gly Thr Pro
1               5                   10                  15

Asp Leu Gln Thr Arg
            20

<210> SEQ ID NO 41
<211> LENGTH: 11
<212> TYPE: PRT
<213> ORGANISM: Streptomyces sp. C5

<400> SEQUENCE: 41

Leu Leu Gly Ala Asp Val Asp Asp Leu Met Arg
1               5                   10
```

HONEY PROTEOMICS FOR HONEYBEE DISEASE AND ENVIRONMENTAL BIOMONITORING

CROSS REFERENCE TO RELATED APPLICATIONS

This application claims the benefit of U.S. provisional patent application 62/955,618, filed Dec. 31, 2019, the complete contents of which is hereby incorporated by reference.

FIELD OF THE INVENTION

The invention generally relates to methods for detection of low abundance proteins in a honey sample using a dye-loaded substrate such as nanoparticles or polymer filaments.

BACKGROUND OF THE INVENTION

Honey, a natural product produced by honeybees from the nectar of flowers, has been one of the most appreciated products utilized by humans since antiquity as a result of both its antibiotic properties and nutritional value[1-3]. The protein composition of honey is known to be complex but comprehensive proteomics studies of honey are scarce and mainly focused on bee proteins, dismissing the potential protein contribution of other organisms to the honey proteome. Erban et al.[4] previously described the protein content of a variety of honeys; Di Girolamo et al.[5] successfully described a correlation between the presence of plant proteins and allergens in a variety of honeys. In addition, Kim et al.[6] have shown that honey contains a record of proteins involved in the honeybee stress response.

Given the repertoire of proteins present in honey that have the potential to identify and characterize fluctuating physiologic and pathological states of the bee health, more studies are needed. Although recent studies of Colony Collapse Disorder (CCD) focused on describing the potential causes via analyses of ribosomal RNA from CCD bees[7] and the ecology of the disease[8], the relationship between CCD colonies and their honey proteome still remains unexplored. CCD is a significant cause of concern among beekeepers and contributes to a significant portion of bee mortality rate[8,9]. In 2019, bee mortality in the U.S. increased to a total of 30%[10] due to a combination of environmental factors including known and unknown pathogens (parasites, bacteria, viruses), pesticides, nutritional deficiency of local pollens[11], and additional sources of honeybee stress[12]. The cause and cure of CCD have remained complex and elusive[13].

Honey has a very low protein content (0.1-0.5%),[14] a very high sugar content and a complex composition, a combination that is known to hamper proteomic analysis[4,15]. In previous studies, Di Girolamo et al.[5] used SDS-PAGE to separate honey proteins; Erban et al.[4] utilized Sephadex columns and nanoliquid chromatography (nLC).

New and simpler methods for protein detection in honey are needed. Such methods may allow for diagnostic tests that can detect CCD which would enable the provision of individualized therapy.

SUMMARY

Provided herein are methods of protein isolation and detection in honey samples using multifunctional core-shell nanoparticles having an affinity bait covalently bound to a polymer nanoparticle. When applied to a protein solution, the nanoparticles rapidly capture, concentrate and preserve solution-phase analytes, which can be then measured with standard analytical methods.

The methods described herein may be employed as a general test of colony wellness. The large amount of molecular information derived from the disclosed methods provide a new means of studying environmental exposures (carcinogens, pesticides, non-bee insects, and flower physiology) recorded in the flower pollen within a 10 km radius around the hive. Precise molecular information about bee health can be used to treat colonies before their collapse therefore improving honey production. The methods may also lead to an increase in crop productivity and seed quality due to an increase in honeybee population, and therefore, crop pollination.

An aspect of the disclosure provides a method for isolating proteins from a honey sample, comprising contacting the honey sample with a substrate functionalized with one or more reactive dyes; and recovering proteins associated with the substrate. In some embodiments, the substrate comprises porous nanoparticles or polymer filaments. In some embodiments, the porous nanoparticles are core-shell nanoparticles and the one or more reactive dyes are attached to a surface of the core. In some embodiments, the porous nanoparticles are formed from a poly(N-isopropylacrylamide-co-acrylic acid) core and a poly(N-isopropylacrylamide-co-vinylsulfonic acid) shell. In some embodiments, the one or more reactive dyes are selected from the group consisting of oxazine dyes, dioxazine dyes, benzoxazine dyes, azo dyes, diazo dyes, anthraquinone dyes, phathalocyanine dyes, and chlorotriazine dyes. In some embodiments, the recovering step comprises centrifuging the sample containing the substrate to form a pellet and eluting the protein from the pellet.

Another aspect of the disclosure provides a method of detecting proteins in a honey sample, comprising contacting the honey sample with a substrate functionalized with one or more reactive dyes; recovering proteins associated with the substrate; and determining an amino acid sequence of the proteins. In some embodiments, the amino acid sequence is determined using tandem mass spectrometry. In some embodiments, the proteins are digested to form peptides prior to determination of the amino acid sequence. In some embodiments, the method further comprises a step of assigning the proteins to a taxonomic genus by aligning the amino acid sequence to known protein sequences.

Another aspect of the disclosure provides a method of assessing the risk of colony collapse disorder (CCD) in a bee hive, comprising contacting a honey sample obtained from the bee hive with a substrate functionalized with one or more reactive dyes; recovering proteins associated with the substrate; determining an amino acid sequence of the proteins; and determining that the bee hive is at an increased risk for CCD when the amino acid sequence is from a bee pathogen or a bee stress biomarker, or determining that the bee hive is not at an increased risk for CCD when the amino acid sequence is not from a bee pathogen or a bee stress biomarker.

In some embodiments, the bee pathogen is selected from the group consisting of *Varroa destructor, Paenibacillus* sp., *Ascosphaera apis, Aspergillus* sp., *Nosema ceranae, Tropilaelaps mercedesae*, and *Apis mellifera* filamentous virus. In some embodiments, the bee stress biomarker is a heat shock protein or bee-derived antibacterial peptide. In some embodiments, the method further comprises treating the bee hive for CCD when it is determined that the bee hive is at an increased risk for CCD. In some embodiments, treating the bee hive comprises administering an antimicrobial agent and/or isolating the bee hive from other hives.

DETAILED DESCRIPTION

Figure 1:
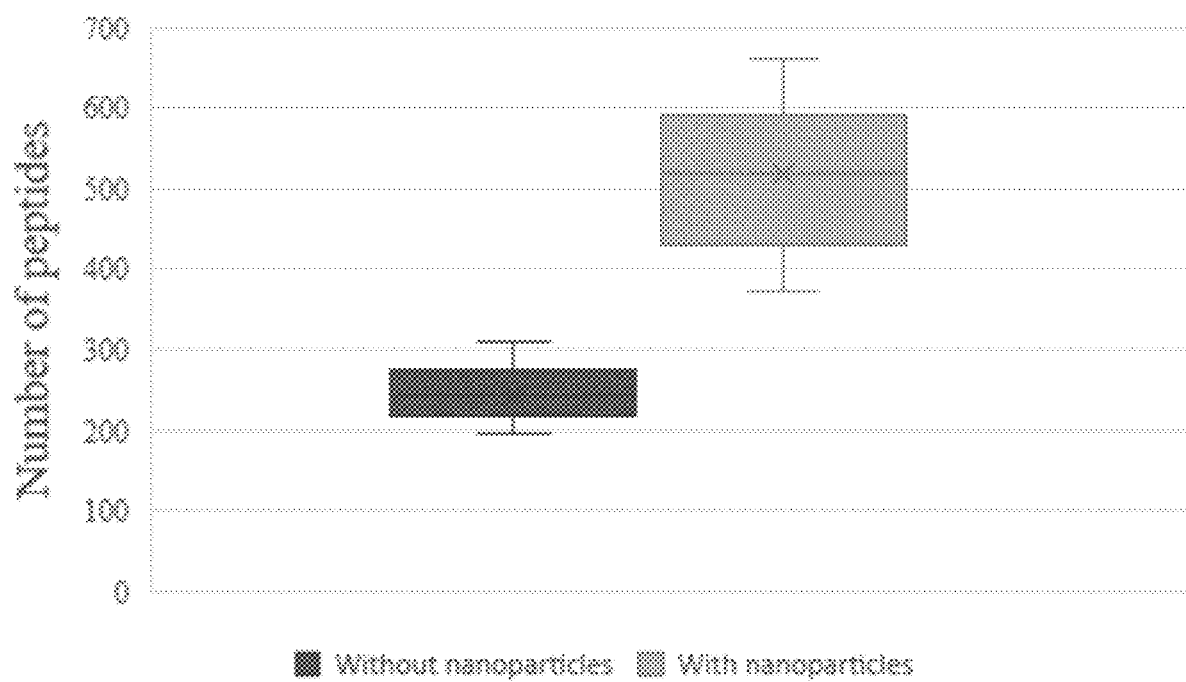
FIG. 1. Number of peptides identified using nanoparticles vs Sephadex columns.

Aspects of the invention relate to nanotechnology-based methods for purifying and concentrating proteins/peptides in honey. Identification of the isolated proteins (e.g. by mass spectrometry) followed by bioinformatics analysis allows for a simple and rapid diagnostic test that can be performed in situ to detect colony stress predictive of an upcoming colony collapse and the potential causative agents for the pending collapse. The test may thus be used for individualized colony therapy. The methods disclosed herein are also useful for analyzing the environmental conditions surrounding a hive. The nanotechnology-based methods described herein are at least 500 times more sensitive than previous methods for protein analysis in honey. Information about bee health can be used to treat colonies before its collapse, improving honey production and increasing crop productivity and seed quality due to increased honeybee population, and therefore, crop pollination.

The term "peptide" as used herein refers to a short polypeptide, e.g., one that typically contains less than about 50 amino acids and more typically less than about 30 amino acids. In some embodiments, peptides referred to herein have at least 7 amino acids.

As used herein, "honeybee" refers to a flying insect within the genus *Apis* of the bee clade, such as *Apis mellifera*, *Apis cerana*, *Apis koschevnikovi*, and *Apis nigrocincta*.

The term "honey" refers to naturally produced honey containing at least a mix of glucose, fructose, water and glucose oxidase enzyme as well as plant derived compounds. As bees digest pollen, soil and water, bits of proteins from other organisms, including fungi, bacteria and viruses also end up in the insects' stomachs and thus in the honey that is produced. The proteins found in honey have a variety of sources. They may come from, for example, the honeybee itself, bee pathogens, bee microbiota, plants (pollen), plant pathogens, plant microbiota, soil microorganisms, human contamination, airborne microbes, and microorganisms present in food waste.

The term "honey type" refers to a honey from a particular plant origin or a blend of plant origins. The term 'plant origin' and 'botanical origin' are used interchangeably and refer to the plant nectar that the honey is derived from as evidenced by the specific compound(s) present in the honey that are derived from the plant.

The methods described herein can detect peptides from a variety of sources. For example, the methods can detect fungal peptides, e.g. from *Arpergillus* sp., *Ascosphaera apis*, *Aureobasidium pullulans*, *Rhodotorula* sp., *Monilinia fructicola*, *Blumeria graminis*, *Diaporthe helianthin*, *Monilinia laxa*, *Penicillium brasilianum*, *Stereum hirsutum*, *Hirsutella minnesotensis*, *Monosporascus cannonballus*, *Ustilaginoidea virens*, etc.; bacterial peptides, e.g. from *Melissococcus plutonius*, *Paenibacillus larvae*, *Serratia mareeseens*, *Klebsiella variicola*, *Pantoea* sp, *Brevibacillus* sp., *Acinetobacter*, *Citrobacter*, *Enterobacter*, *Erwinia*, *Escherichia*, *Gluconobacter*, *Klebsiella*, *Pseudomonas*, *Agrobacterium* sp. *Burkholderia glumae*, *Flavobacterium* sp., *Glaesserella parasuis*, *Helicobacter pylori*, *Mycoplasma auris*, *Pantoea* sp, *Pectobacterium* sp., *Pseudomonas syringae*, *Streptomyces* sp., and *Xanthomonas* sp in addition to peptides from *Clostridium*, *Bacillus*, and *Streptococcus* genera or from gut microbiota such as *Bartonella* sp., *Lactobacillus* sp., *Snodgrassella alvi*, *Nocardiopsis alba*, Gammaproteobacteria bacterium, Enterobacteriaceae bacterium, *Gilliamella apicola*, *Bifidobacterium* sp., *Bartonella apis*, *Parasaccharibacter apium*, and *Frischella perrana*; viral peptides, e.g. from Darwin bee virus 6, *Apis mellifera* filamentus virus, Robinvale bee virus 2, Deformed wing virus, etc.; parasitic peptides, e.g. from *Varroa destructor*, *Tropilaclaps mercedesac*, *Aethina turnida*, etc.; and plant-derived peptides, e.g. sunflower, lilac, potato, mandarin, olive, red clover, tomato, etc., belonging to classes such as Viridiplantae, Liliopsida, Pinopsia, and Magnoliopsida. The honey sample can thus provide information regarding the types of flowers and allergens within the honeybee collection area. In some embodiments, the collection area comprises an area up to a 10 km radius from the hive location.

In some embodiments, a substrate as described herein comprises dye-functionalized core and core-shell nanoparticles that are used to extract and concentrate the proteins in the honey through size exclusion and affinity interactions. In some embodiments, the nanoparticles are as described in US 20090148961 incorporated herein by reference. Functionalized nanoparticles have pores through which proteins migrate from the solution to the particle and affinity moieties that work as hooks preventing escape of the peptides from the particle during the extraction process.

In certain embodiments, the nanoparticles are comprised of a molecular sieve material. By this, it is meant that the material is porous, lattice-like, honeycombed, or has other properties that permit proteins of a defined molecular mass or weight to enter. The size of the sieve pore is a determinant of whether the protein can penetrate the nanoparticle. The particle, itself, can be of any suitable size, e.g., 1 nm or less; from about 1 nm-100 µm; from about 5 nm-50 µm; from about 10 nm-20 µm; from about 10 nm-10 µm; including any and all values in between. The particles may have any suitable shape, including, but not limited to, spheres, tubes, branched structures, polyhedrons and micro-fluidic valves.

Pores in the sieve material can be designed based on the provided methods to diameters necessary for exclusion of unwanted molecules. Average pore sizes of between about 2 to about 20 nm, 1 nm to 1 μm, 1 nm to 10 nm, 1 nm to 50 nm, 10 nm to 50 nm, 50 nm to 100 nm, 10 nm to 200 nm, 50 nm to 500 nm, 1 nm to 10 nm, 1 nm to 5 nm, and other ranges are envisioned.

The sieve materials used in constructing the nanoparticles may be designed so as to allow only proteins of a certain size to enter the nanoparticles. The size cutoff of the nanoparticles will be dependent on the manner in which the particles are to be used. The cutoff size, as used herein, is meant to describe the approximate size of a protein which is able to enter the nanoparticle. For example, molecular weight (MW) cutoff size of 50 kDa means that molecules of approximately 50 kDa or less in size will be able to enter the nanoparticles, while molecules of approximately more than 50 KDa will be excluded from the particles. In certain embodiments, the particles may have a MW cutoff size of from about 5 kDa to about 100 kDa, although particles having other MW cutoff sizes outside of this range are also contemplated.

In some embodiments, the sieve materials used in constructing the nanoparticles are designed so as to allow all proteins present in the sample to enter the nanoparticles while excluding macromolecules such as such as sugars and inorganic compounds.

In some embodiments, the nanoparticles are formed from polymers made of: acrylamide and derivatives thereof, N-isopropylacrylamide (e.g., Jones and Lyon, Macromolecules, 36:1988-1993, 2003; Jones and Lyon, Macromolecules, 33:8310-8306, 2000) and other N-alkyl substituted acrylamides; N,N-methylenebisacrylamide, N,N-cystaminebisacrylamide, N-vinylalkylamides, acrylic acid, methacrylic acid, allylamine, styrene, benzyl glutamate, 2-ethylacrylic acid, 4-vinylpyridine, silicone, hydroxyethyl methacrylate, ethylene oxide, butylenes terephthalate, 2-acrylamido-2-methyl-1-propanesulfonic acid, vinylpyrrolidone, and ethylene-vinyl acetate. The polymers may or may not be made up of crosslinkable units. In the case of crosslinkable polymers, the crosslinks may be formed either permanently or reversibly. The polymers may be polymers having a single repeating unit or may be co-polymers having two or more monomer units which are included in the polymer. The nanoparticles can be prepared routinely by methods known in the art or as described in any of the above-mentioned references.

In some embodiments, the nanoparticles are formed from an N-isoproylacrylamide (NIPAm), acrylic acid (AAc) copolymer whose pendant carboxylic acid groups are functionalized with an affinity dye having affinity for proteins and peptides, e.g. affinity dyes that are used for dye affinity chromatography. Amino-containing dyes can be added via zero-length cross-linking amidation reactions. In certain other embodiments, the particles have a core made of a NIPAm AAc co-polymer that is surrounded by a shell polymer layer, e.g. made up of only NIPAm or made up of poly(N-isopropylacrylamide-co-vinylsulfonic acid). The shell selectively prevents unwanted entry of larger molecules without hindering the penetration of small proteins and peptides. Proteins and peptides enter the core to be captured with high affinity by dyes immobilized in the core. The nanoparticles provide an effective amplification of the protein/peptide concentration, enabling analysis, e.g. via mass spectrometry (MS), of proteins/peptides that were previously undetectable in honey.

In some embodiments, a substrate as described herein comprises polymer filaments, e.g. non-water involving polymer filaments, that are functionalized with a reactive dye. Suitable polymer filaments include, but are not limited to, nylon filaments, fiber-like polymeric materials, poly(acrylic acid-co-acylamide), poly(methyl methacrylate), acetate polymer, polyester, acrylic fiber, poly(vinyl alcohol), polyurethane, acrylic acid, cellulose acetate, nitrocellulose, nylon polyamide, PLA synthetic fiber, PLGA synthetic fiber, polyacrylamide, polyacrylimide, and polyhydroquinonediimidazopyridine. In some embodiments, the substrate comprises glass wool.

An affinity dye (also referred to herein as an organic dye or a reactive dye) can bind proteins either by specific interactions at the protein's active site or by a range of non-specific interactions (e.g. binding to glycosylated protein molecules). Peptides attach reversibly to these dyes to be extracted and can be released in a smaller volume increasing protein concentration. Without being bound by theory, it is thought that the high-affinity binding of such dyes to proteins is based on hydrophobic and electrostatic forces. The specificity of the dye-protein interaction depends mainly on hydrophobic interactions, whereas electrostatic forces contribute to the stability of interaction. The dye binding site on the surface of the target protein is a nonpolar pocket surrounded by hydrophilic amino acid residues. Moreover, the protein binding sites are often located in areas overlapping with the binding sites of biological ligands with respect to other parts of the protein surface. Organic reactive dyes can insert aromatic rings into nonpolar hydrophobic pockets of the protein surface, while the flanking portions of the dye and protein molecules can rearrange, depending on energy constraints. Since both active protein sites and dye molecules have limited conformational freedom, some specificity is achieved.

Increasing the size of the dye molecule ring system can enhance the specificity. For example, Cibacron Blue F3GA forms a strong bond with specific classes of enzymes (dehydrogenases and kinases) because the 1-amino-4-(4'-aminophenylamino)-anthraquinone-2,3'-disulfonic acid part of the dye fits well to a structural element of the enzyme called the dinucleotide binding fold. In addition to high specific binding of some classes of proteins, Cibacron Blue F3GA also forms nonspecific complexes with additional proteins. This latter attribute is most likely due to the ability of the dye to act as weak cation exchanger through its sulfonic groups. It is contemplated that all ionic aromatic compounds are capable of binding all classes of proteins and peptides that have a sufficiently large exposed hydrophobic region Although dyes are all synthetic in nature, they are still classified as affinity ligands because they can interact with the active sites of many proteins mimicking the structure of the substrates, cofactors, or binding agents for those proteins. A number of textile dyes, known as reactive dyes, have been used for protein purification. Most of these reactive dyes consist of a chromophore (either azo dyes, anthraquinone, or phthalocyanine), linked to a reactive group (often a mono- or dichlorotriazine ring). The interaction between the dye ligand and proteins can be by complex combination of electrostatic, hydrophobic, hydrogen bonding.

Suitable dyes include, but are not limited to, oxazine dyes, dioxazine dyes, benzoxazine dyes, azo dyes, diazo dyes, anthraquinone dyes, phthalocyanine dyes, chlorotriazine dyes, anionic dyes, and cationic dyes. More specifically, suitable dyes include, but are not limited to, those dyes shown in FIG. 7. In preferred embodiments, the dye is Bismarck Brown Y or Trypan blue.

Methods disclosed herein include contacting a honey sample with nanoparticles under conditions effective for the nanoparticles to reversibly and selectively trap proteins/peptides of a defined molecular mass or particle size. In some embodiments, the honey sample is diluted, e.g. with deionized water or an appropriate buffer, prior to the contacting step. In some embodiments, the honey is diluted in a ratio of 1 g of honey to 1-3 ml of water/buffer. In some embodiments, the sample is heated and/or sonicated to aid in dissolution.

After the honey sample is contacted with the nanoparticles, proteins associated with the nanoparticles may be recovered. In some embodiments, the recovering step may comprise centrifuging the sample containing the porous nanoparticles to form a pellet, washing the pellet, and eluting the protein from the pellet. The protein may be resuspended in an appropriate buffer or water, and in some embodiments, reduced and digested to provide peptides.

Further embodiments provide methods of detecting the protein comprising an additional step of determining an amino acid sequence of the proteins that were recovered. In some embodiments, a combination of high-performance liquid chromatography (HPLC) and mass spectrometry (MS) analysis is used for detection and identification of amino acid sequence in the sample. The peptides are ionized prior to introduction into the mass spectrometer. Tandem spectra are acquired and, based on the intensity of the peaks, database searching can identify peptides present in the honey sample.

Other analytical methods known in the art can be employed such as nuclear magnetic resonance, infrared spectroscopy, solid phase immunoassay (e.g. ELISA and the like) immunoprecipitation, colorometric assay, radiometric assay, fluorescent assay, flow bead/flow cytometry, western blotting, protein sequencing and any chemistry analytic method for analysis of proteins.

Bioinformatics analysis may be used to identify the organism of origin of the protein by aligning the amino acid sequence to known protein sequences, e.g. as found in the NCBI protein database.

In some embodiments, tandem mass spectra are analyzed using a de novo peptide sequencing feature which can identify an amino acid sequence from a mass spectrum without the use of a database. Alternatively, or in addition, the analysis may be performed by creating a database with protein sequences that belong to organisms of interest, for example, the proteome of the honeybee, honeybee pathogens, pollen allergens, and flower pathogens.

Once the bioinformatics analysis is completed, a full protein report may be created including, but not limited to, details about peptides found, protein of origin, organism of origin, bee stress biomarkers such as heat shock proteins, and the environmental conditions in the hive surroundings such as pollen particles, allergens, and plant pathogens. The method provides the honey's molecular recording of all the fluctuating physiologic or pathological states of the bee health and also all the flowers, the environmental pathogens, and the pesticides in the local vicinity, e.g. a radius of up to 10 km, of the colony. Honey contains pollen, allergens, plant pathogens, nectar of all the plants, and the pesticides in the bodies of water that the honeybee has been in contact with throughout the season of food collection (spring and summer). Information regarding plant pathogens may be used to diagnose health of nearby crops and allow for more immediate treatment of crops if needed.

Embodiments of the disclosure also provide methods of diagnosing diseases that affect honeybees. Most of the pathogens that affect honeybee colonies are present throughout the year and coexist in the hive as parasites. For example, *Apis mellifera* has two different populations within the year: short-living summer bees and long-living bees that make their way through the winter. Because of the harsh winter conditions, the majority of colony collapse disorder (CCD) occurs during the winter when bees are immunosuppressed and the population is considerately smaller than in the summer. Considering that honey starts being produced during the spring, a sample of honey extracted from a colony can help to drastically reduce honeybee mortality and, therefore, increase the pollination of flowers and increase honey production. Honey contains a record of all the parasites and microorganisms (harmful or not) that live in the hive throughout the year. The methods described herein can be used to detect both the proteins that come from such parasites and honeybee stress biomarkers.

It may be determined that the bee hive is at an increased risk for CCD or other diseases when the amino acid sequence detected is from a bee pathogen or a bee stress biomarker. In some embodiments, the bee pathogen is selected from the group consisting of *Varroa destructor*, *Paenibacillus* sp., *Ascosphaera apis*, *Aspergillus* sp., *Nosema ceranae*, *Tropilaelaps mercedesae*, and *Apis mellifera* filamentous virus. In some embodiments, the bee stress biomarker is a heat shock protein or bee-derived antibacterial peptide such as hymenoptaecin which may be used to early diagnose potential diseases since it is one of the broad-spectrum antibiotics secreted when the bee contracts a pathogen. Defensin-1 is another peptide produced by the bee when an infection is occurring. Other bee-derived antibacterial peptides include, but are not limited to, apidaecins, abaecin, apamin, melittin, and royal jelly proteins.

In some embodiments, the methods described herein further comprise treating the bee hive for CCD or other diseases when it is determined that the bee hive is at an increased risk for CCD or other diseases. In some embodiments, treating the bee hive comprises administering an antimicrobial agent and/or isolating the bee hive from other hives. Suitable therapies include, but are not limited to, administering an antimicrobial agent or antibiotic such as fumagillin, oxytetracycline, tylosin, terramycin/powdered sugar mixture, administering a mite control agent such as formic acid, oxalic acid, fluvalinate, sucrose octanoate, individual or joint administration of thymol, eucalyptol, menthol, and camphor. Other measures include isolating a collapsing colony from other healthy colonies. If needed, proper therapies may be provided to treat the colony before winter arrives.

In some embodiments, the honey sample is obtained from a colony that is suspected of having been exposed to a pathogen or other stress-inducer (e.g. pesticides, nutritional deficiency, starvation, dehydration, pollutants, overexposure to UV light, etc.), or at risk for being exposed to a pathogen or other stress-inducer. In other embodiments, the honey sample is obtained from a healthy colony. In some embodiments, honey samples are obtained from a colony several times, e.g. weekly or monthly, for continued monitoring of the health of the colony. In some embodiments, the methods disclosed herein are used to monitor efficacy of treatment of bee colonies.

The methods disclosed herein can also be used as a monitor for the ecosystem health and molecular changes in the surroundings of the hive where the honey sample come from. Early detection of plant-pathogens during the pollination season will allow crop producers to implement early treatment before the harvest in the summer. The methods may also be used by researchers that focus on crop and seed improvement.

In further embodiments, the methods described herein may be used to validate the source and quality of the honey, e.g. by determining which flower/pollen proteins are in the honey. For example, the test may distinguish between different honey types including, but not limited to, Manuka, Pasture, Ling Kahami, Portobello, Greek Pine, Yorkshire, Chilean Ulmo, Chilean Rain Forrest, Australian *Eucalyptus*, Himalayan, Scottish Heather, Scottish Wild Flower, English Heather, English Wildflower, New Zealand Clover, Australian Clover, Cuban Comparitan, Acacia, Spanish Blossom, Tasmanian Leatherwood, Organic Honey All, New Zealand Beach, Kanuka, New Zealand Bush, New Zealand Honey Dew, Jarrah, Thyme, Kamahi and *Leptospermum* honeys of all varieties.

In other embodiments, counting pollen peptides in local hives could indicate when hay fever is likely to flare in the area, thus benefitting allergy-sufferers.

In further embodiments, analysis of plant virus proteins found in the honey provides an indication of the types of diseases that are infecting local crops.

Embodiments of the disclosure also provide a kit with nanoparticles/probes as described herein and optionally any appropriate buffers. In some embodiments, the incorporated dyes bind to selected proteins (e.g. proteins commonly found to be markers of colony stress or disease). The kit may further comprise components for honey sampling from a hive/colony. In certain embodiments, the nanoparticles are provided in a form suitable for use in purification or diagnostic methods. Kits generally provide the nanoparticles as well as reagents, instructions, and the necessary products for performing the purification or diagnostic method.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example 1

Summary

We analyzed 15 honey samples collected from healthy and collapsing hives in Virginia, Maryland, and Argentina using affinity sample concentration, tandem mass spectrometry, and a peptide authentication bioinformatics pipeline. Specificity was defined by sequence identity with an organism at the genus or species level, evolutionary taxonomic verification for related clades, and lower homology with other organisms. We identified, for the first time, 9855 low-abundance honey peptides deriving from 1381 organisms including the five most relevant bee pathogens and the top 10 most pathogenic bacteria in plants. The most represented organism was *Apis mellifera*, followed by honeybee microbiota (e.g. *Lactobacillus kunkeei, Gilleamella apicola*), plants (e.g. *Solanum* sp., *Vitis vinifera*), and plant pathogens (e.g. *Agrobacterium* sp. *Burkholderia glumae, Erwinia* sp., *Flavobacterium* sp., *Glaesserella parasuis, Helicobacter pylori*). Diseased hives yielded stress markers (e.g. *Apis mellifera* heat shock proteins) and honeybee pathogens peptides (e.g. *Varroa destructor, Aspergillus* sp., *Ascospaera apis*). The present study showed that honey can be used as a tool for honeybee disease diagnostic and environmental biomonitoring.

Materials and Methods

Experimental design: Fifteen honey samples from *Apis mellifera* hives were used for this study. Twelve honey samples came from Northern Virginia local hives, one honey sample was from Southern Maryland, and two samples were from Mar del Plata, Argentina. Each sample was diluted with deionized water, concentrated with affinity nanoparticles, trypsin digested, and subjected to LC-MS/MS analysis.

p-NIPAm-co-AA core synthesis: The p-NIPAm-co-AA core was synthesized via precipitation polymerization reaction. 4.750 gr of NIPA and 0.4 gr of BIS were dissolved in 500 ml of deionized water, then the solution was vacuum filtered using Millipore® type HAWP, pore size of 0.45 µm. The filtered solution was purged with nitrogen at room temperature and medium rate stirring for 30 min, and then 0.525 g of AA were added. The solution was purged for 15 min under nitrogen under room temperature and then heated for 30 min at 70° C. Once stabilized, 0.276 g of KPS dissolved in 5 ml of deionized water were added for the polymerization reaction to start and hold overnight. Then while stirring, the solution was cooled down at room temperature. The nanoparticles were posteriorly washed and centrifuged using Eppendorf 5415R centrifuge in aliquots of 1 ml. at 16,200 rpm for 50 min discarding the supernatant 5 times. The nanoparticles were resuspended in 1 ml of deionized water.

p-NIPAm-co-AAc core functionalization: An aliquot of 1 ml of p-NIPAm-co-AAc particles containing 20 µl of a 10% saline solution was centrifuged for 30 min at 20° C. and 16,100 rcf. The supernatant was removed and resuspended in 500 µl of buffer 0.2M $NaH_2PO_4$. The solution was transferred to a round-neck flask and stirred. Posteriorly, a solution containing 150 mg of N-hydroxysuccinimide and 260 mg of 1-Ethyl-3-(3-dimethylaminopropyl)carbodiimide in 3 ml of $NaH_2PO_4$ 0.2 M was added to the flask and held for 15 min at 20° C. The solution was aliquoted out to a 2 ml tube and centrifuged for 20 min. The supernatant was removed, and the nanoparticles were resuspended in 500 µl of buffer containing 27 g of $Na_2HPO_4$ and 1.17 g $NaH_2PO_4$. The solution was centrifuged, and the supernatant was removed and transferred to a round-neck bottle. 0.2 g of Bismarck Brown Y was dissolved in 210 ml of a solution containing 27 g of $Na_2HPO_4$ and 1.17 g of $NaH_2PO_4$ and vacuum filtered. Posteriorly, the Bismarck Brown Y solution was added to the round-neck bottle containing the nanoparticles and held overnight while stirring. The functionalized nanoparticles were washed with centrifugation 19,000 rpm for 45 min for 5 cycles. The same process was carried out to functionalized nanoparticles with 0.2 g of Trypan Blue.

p-NIPAm-co-AAc core-shell synthesis: 20 ml of NIPA/AAc/Bismarck Brown were added into a round-bottom flask, connected to an Allihn condenser. The solution was kept at 75° C. and purged with nitrogen for 1 hr. The shell solution was prepared dissolving 0.156 g of NIPA, 0.020 g of BIS (N-Isopropylacrylamide), 26 µl of VSA, and 0.092 g of KPS (Potassium Persulfate) into 20 ml of deionized water, and posteriorly filtered. The shell solution was added to the NIPA/AAc/Bismark Brown Y at a drop rate of 1 drop per second. The reaction was held for 3 hours at 75° C. and continuous stirring and posteriorly cooled down until achieving room temperature. The particles were washed by centrifugation 19,000 rpm for 50 min for 5 cycles.

Sample preparation: The honey samples were diluted using deionized water in a ratio of 1 g of honey to 2 ml of water. The honey/water solution was placed in a water bath at 40° C. for 15 min until complete dissolution and then the samples were sonicated for 5 min at ultrasonic power of 60 kW. 75 µl of NIPAm/AAc/Bismarck Brown were added to 1 ml of the honey/water solution and incubated for 30 min in the rotator at room temperature. 25 µl of NIPA/AAc/Trypan Blue were added to the solution and incubated for another 30 min in the rotator at room temperature. The solution was centrifuged for 15 min at room temperature at 16.1 ref. The supernatant was discarded, and the pellet was resuspended using 500l deionized water 3 times. The pellet was finally resuspended in 60 µl of elution buffer solution containing 4 g of SDS, 95 µl of $NH_4HCO_3$ 50 mM, and 5 µl TCEP and incubated for 20 min on a rotator. The samples were centrifuged at 16.1 rcf for 20 min at room temperature and the supernatant was placed in a new tube containing 414 µl of 50 mM $NH_4HCO_3$. Then, the samples were cleaned using Pierce Detergent Removal Spin Column (Thermo Scientific) following manufacturer instructions. Once clean, the samples were prepared for trypsin digestion adding 4.6 µl of DTT (15.4 mg/90 µl deionized water to each sample and incubating in 37° C. water bath for 30 min. Then, 30 µl of iodacetamide (18.5 mg iodacetamide in 200 µl deionized water) were added, and the samples were incubated in the dark for 20 min. After incubation, 2.3 µl of Trypsin were added and incubated overnight at 37° C. The next day, 2.3 µl of TFA were added to stop the trypsin. Finally, the samples were clean using Pierce C18 Spin Columns following manufacturer instructions and stored at −80° C.

Mass spectrometry analysis: The samples were analyzed with an Orbitrap Fusion™ Tribrid™ Mass Spectrometer (Thermo Scientific, Waltham, MA) coupled with a nanospray EASY-nLC 1200 UHPLC. Reversed-phase chromatography separation of the peptide mixture is performed using PepMap RSLC 75 µm i.d.×15 cm long with 2 µm, C18 resin LC column (ThermoFisher). 0.1% formic acid as mobile phase A, and 0.1% formic acid, 80% acetonitrile mobile phase B are used. Sample-peptides are eluted using a linear gradient of 5% mobile phase B to 50% mobile phase B in 90 min at 300 nL/min, then to 100% mobile phase B for an additional 2 min. The Thermo Orbitrap Fusion™ Tribrid™ Mass Spectrometer (Thermo Scientific) was operated in a data-dependent mode in which each full MS scan is followed by TopN MS/MS scans of the most abundant molecular ions with charge states form 2+ to 4+ were dynamically selected for collision-induced dissociation (CID) using a normalized collision energy of 35%.

Bioinformatics analysis: High-confidence peptide identifications were obtained by applying the following criteria: 1) Xcorr >2.0, >3.0 and >4.0 for 2+, 3+, 4+ precursor ions; 2) q-value <0.05; and 3) probability of randomized identification: e0.01. Acceptable false discovery rate (FDR) based on forward-reverse decoy was <1%. Peptide identification was performed using Peaks® X (Bioinformatics Solutions Inc.)[18] integrating de novo sequencing and database search to determine the honey proteome. Spectra were searched against a database including the following species *Apis mellifera*, honey bee pathogens (HoloBee Database v2016.1[25]), pollen allergens (the Structural Database of Allergenic Proteins[53] and the allergen names from the IUIS website[54]), and plant pathogens extracted in FASTA format from ncbi.nlm.nih.gov/. The output list of peptides was authenticated by BLAST analysis (blast.ncbi.nlm.nih.gov/Blast.cgi)[19] using a novel Python script called HONEYMETER. The Honeymeter pipeline includes the following steps: 1) retain peptides with sequence greater than 7 amino acids, 2) peptide attribution to an organism at the species or genus level via BLAST analysis, 3) cross validation with other organisms whereby the peptide is retained if other organisms have 10% lower homology, 4) taxonomy verification within the evolutionary clade: if parent protein has >60% similarity with proteins within the closest 10 organisms the peptide is retained. For this analysis, the following criteria were applied: Percent Identity=95%, Query Cover=100%, E value <10-4 where the peptide alignment was unambiguous; the peptide was not assigned to more than one protein or genus-species.

Results

Improving methods for molecular analysis of honey is critical in order to maximize the utility of honey as a diagnostic biorepository. Here, we have applied an affinity concentration technology and a bioinformatics pipeline that captures and concentrates honey proteins and provides sequence data with high analytical sensitivity and 95% accuracy.

Data analysis from the 15 honey samples yielded a total of 9855 authenticated peptides assigned to 1381 species including *Apis mellifera*. A comparison of proteins of honeybee origin in honey samples purified using Sephadex columns versus nanoparticles, showed that the use of nanoparticles increased the sensitivity of the method by 2-fold (FIG. 1). The honey samples differed greatly in initial protein concentration but honey samples that contained a high protein content did not necessarily yield a high number of peptides. The absence of a direct correlation between protein concentration and identifiable peptides could be due to a poor quality of the peptides. It should be noted that minimal peptide length was set to seven amino acids, shorter peptides were discarded. Old or poor-quality honeys containing a high concentration of short peptides could have been affected by this criterion.

Also, extraction of the protein content with high sensitivity and specificity using affinity nanoparticles and bioinformatics authentication allowed us to access the multi-species molecular content of honey. Previous studies showed that proteins in the honey are mostly bee-secreted[20,21]; however, pollen, plant proteins, and pollen-related microbes have also been found[1] proving that honey bees act as contact biosensors as they consume environmental peptides from numerous sources that make their way into honey.

Affinity Nanoparticles Increase the Analytical Sensitivity of Mass Spectrometry Analysis.

To optimize the experimental workflow, we compared two pre-analytical processing methods: affinity nanoparticle concentration and Sephadex columns. We found that the use of affinity nanoparticles increased 2-fold the peptide identification in the honey samples. Particularly, the identification of peptides from *Apis mellifera* yielded an average of 518.6±94.42 using affinity nanoparticles while the average for Sephadex columns was 244.7±39.43 (FIG. 1).

This difference relies on the sensitivity and efficacy of the methods. While Sephadex columns clean up the honey extracting salt, sugars, and low molecular weight molecules, the dye-functionalized core and core-shell nanoparticles extract and concentrate the proteins in the honey through size exclusion and affinity interactions. Functionalized nanoparticles have pores through which proteins migrate from the solution to the particle, and affinity moieties that work as hooks preventing escape of the peptides from the particle during the extraction process. Also, Bismarck Brown Y and Trypan Blue were used as ligands to increase the affinity between the peptides and the nanoparticles because of their versatility in protein binding. Peptides attach reversibly to these dyes to be extracted and released in a smaller volume increasing protein concentration.

Figure 2:
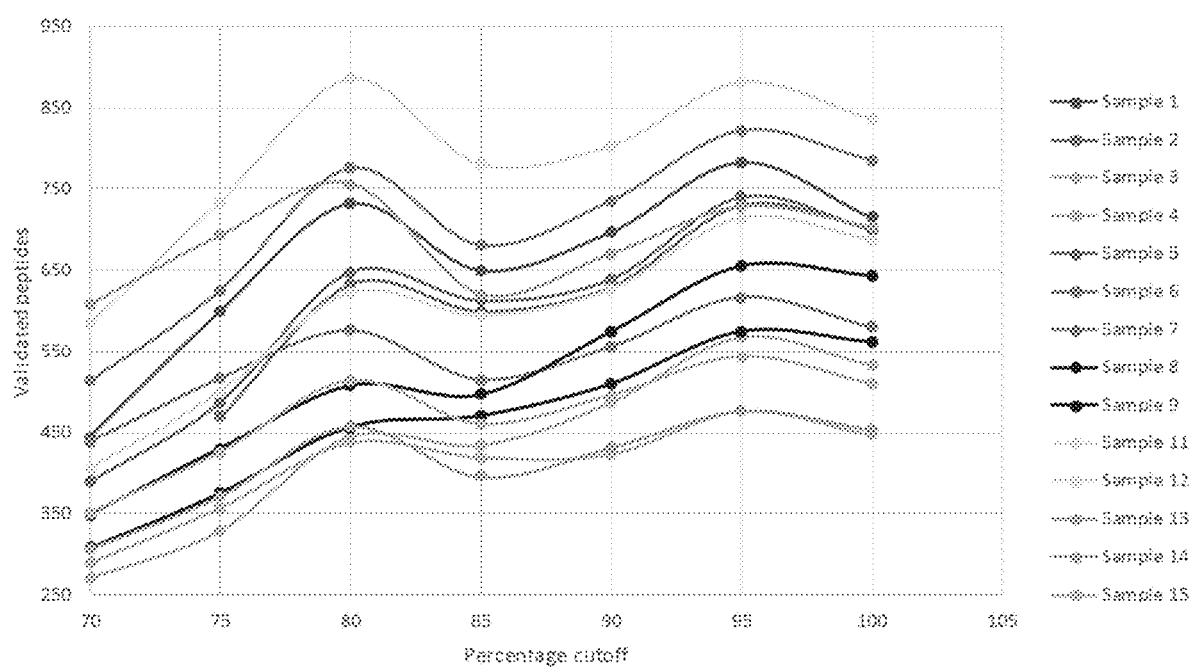
FIG. 2. Peptide yield in function of the homology threshold. 95% homology threshold yields the highest number of peptides.

Bioinformatics Sequence Authentication and Database Annotation Verification Increase Specificity of Peptide Attribution Peptide identification in environmental and microbiome studies is greatly affected by the quality of proteomic database annotation. In this study, we developed a novel bioinformatics pipeline, called Honeymeter, to authenticate database-derived and de-novo sequenced peptides (Peaks Studio). The pipeline included four steps: a peptide was authenticated if all the following four conditions were met: 1) sequence was greater than 7 amino acids, 2) attribution to an organism at the species or genus level according to a sliding homology threshold, 3) all other organisms had 10% lower homology, and 4) the parent protein had >60% homology in the 10 taxonomy closest organisms within the evolutionary clade. Iteration of the algorithm with different homology threshold cut off demonstrated that the highest number of peptides are authenticated with 95% homology (FIG. 2). A sliding homology threshold enables the identification of peptides that can partially obviate to database annotation issues.

The Honey Proteome Represents 1381 Organisms

Figure 3A:
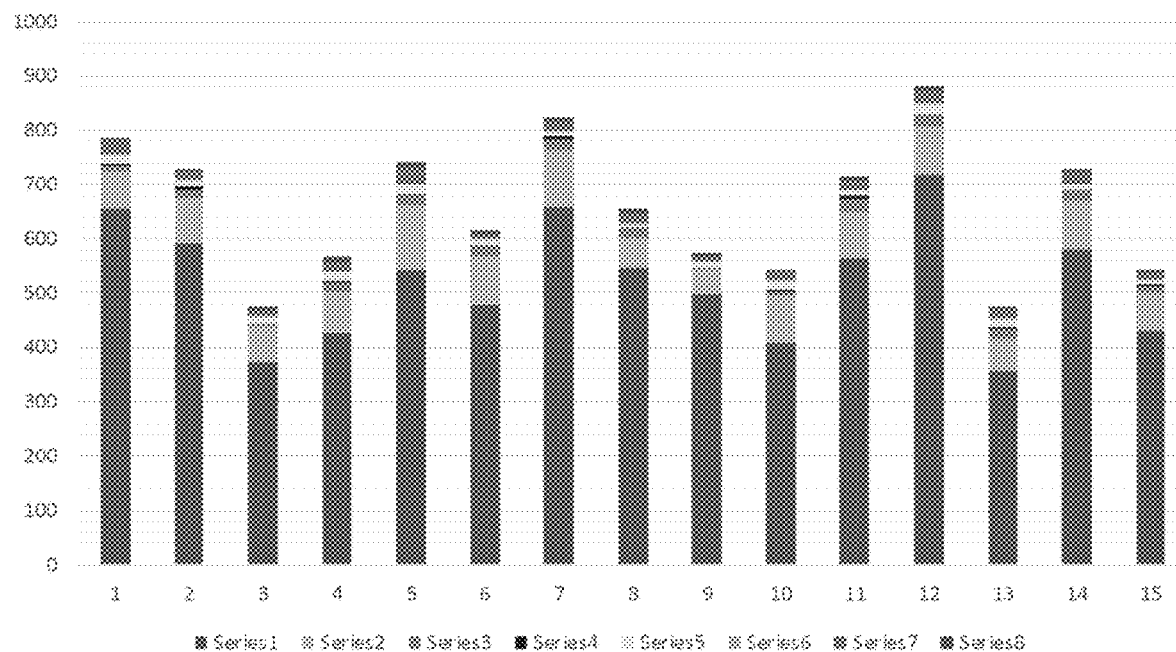
FIGS. 3A-B. (A) Stacked bar plots representing the total number of peptides per sample, and the number of peptides from *Apis mellifera*, Bacteria, Fungi, and Plant taxa, Arachnida, and Insecta class, viruses, and others. (B) Classification and diversity of the organisms found in honey samples.
Figure 3B:
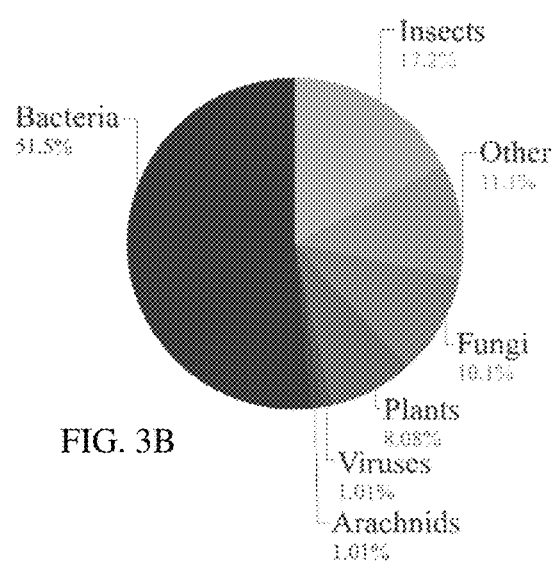

Analysis of the peptide abundance by group of organisms was performed. As expected, most of the peptides detected in this study derived from *Apis mellifera* (FIG. 3) with an average of 79.41% and a coefficient of variation of 20.32%. The large abundance of honeybee peptides is consistent with the protein secretion performed by the bee to adjust the final protein concentration of the honey[1]. Also, the high coefficient of variation (CV) indicates a strong disparity among the samples. Multiple factors could have contributed to this variation. In a first instance, the initial protein concentration differed among the samples reflecting this variation on the results. Secondarily, a differential affinity between the dye-functionalized core-shell nanoparticles and the honey proteins could affect the yield of the extraction process. Differentially captured analytes are the result of size exclusion and affinity interactions between the nanoparticle and the honey proteins.

The stacked column plot (FIG. 3) also shows that peptides from bacteria and fungi ranked as the most abundant after honeybee peptides with an average of 12.32% and 2.37% respectively. In both cases, the coefficient of variation was high, bacteria presented a CV of 23.36% while fungi presented a CV of 42.63%. We hypothesized that the large number of bacterium and fungus peptides present in the honey derive from the microbiome of the pollen and the water bodies that the bees come in contact with during pollen and water collection[22]. Pollen is the most nutritional and indispensable source of protein the bee relies on; however, pollen protein and microbiome composition fluctuate from species to species[23,24]. We found that most of the bacteria and fungi identified in the honey samples are known to be present in the honeybee as part of its microbiome[25] or in the environment whether in water or soil[26-28]. The presence of these microorganisms proves that honey could be utilized as an environmental biomonitor of the ecosystem and bee health.

Also, we performed a statistical analysis of the number of organisms identified per sample. We found that there is not a significant correlation between peptide abundance and diversity of species. Although *Apis mellifera* contributed the most to the honey proteome (FIG. 4), bacteria are the most diverse group, constituting an average of 51.2% of the total identified species. These results agree with previous microbiology reports of honey[29,30]. Unexpectedly, just 8.08% of the species identified in this study belong to the plant kingdom. We observed that a significant number of plant peptides were discarded in our bioinformatics pipeline. When the amino acid sequence is conserved among multiple genera the peptide is discarded; however, this could suggest a taxonomic relationship[31] among the pollen proteins contained in the honey, and therefore among their plants.

Honey is a Source of Colony Stress Biomarkers.

In this study, data evaluation from the 15 honey samples yielded the identification of 7840 peptides unambiguously assigned to *Apis mellifera*. Most of these peptides were secretory proteins known to be present in the honey such as venom related proteins, royal jelly related proteins, glucose dehydrogenase, and isoforms. Heat shock proteins are known to be secreted in the head and the abdomen when the honeybee is exposed to stress conditions, indicative of a stress response to biotic and abiotic stressors such as dehydration, starvation, UV overexposure, pesticides, and pathogens[6], functioning as a stress biomarker. Importantly, bee stress response proteins identified in the honey offer a comprehensive portrait of the colony as a whole and would be more effective than past attempts using individual bee necropsies. Also, honey provides a non-invasive material to monitor the colony health at the super-organismal hive level without sacrificing an excessive number of bees to reach a population-representative sample.

Figure 4:
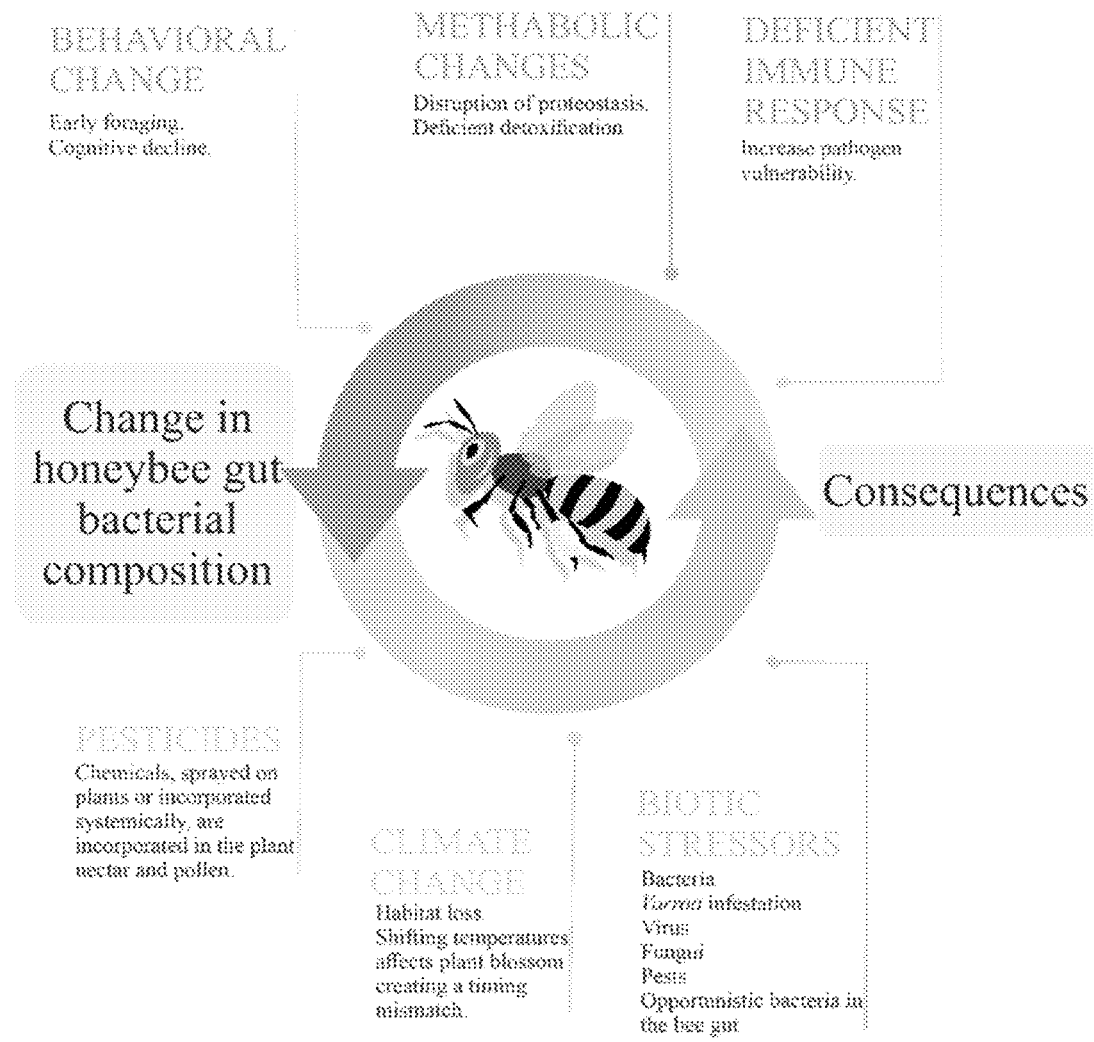
FIG. 4. Stressors that affect honeybee microbiome and their consequences.
Figure 5:
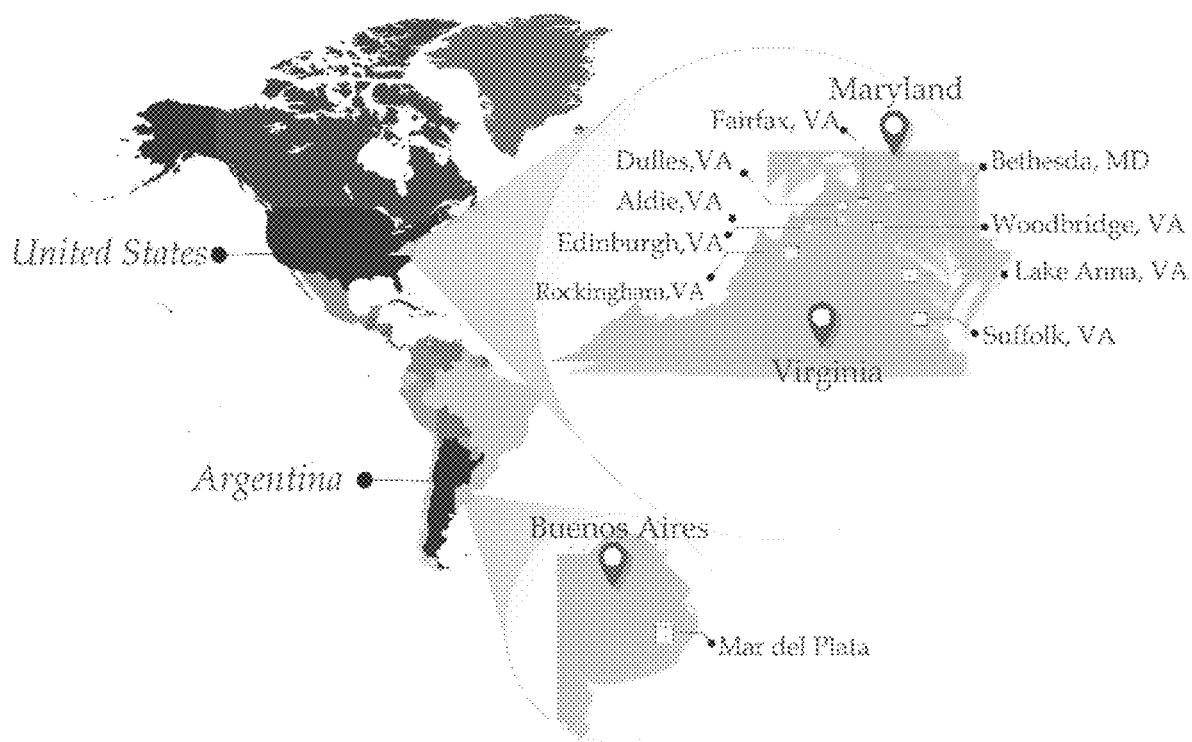
FIG. 5. Geographical distribution of honey samples.
Figure 6:
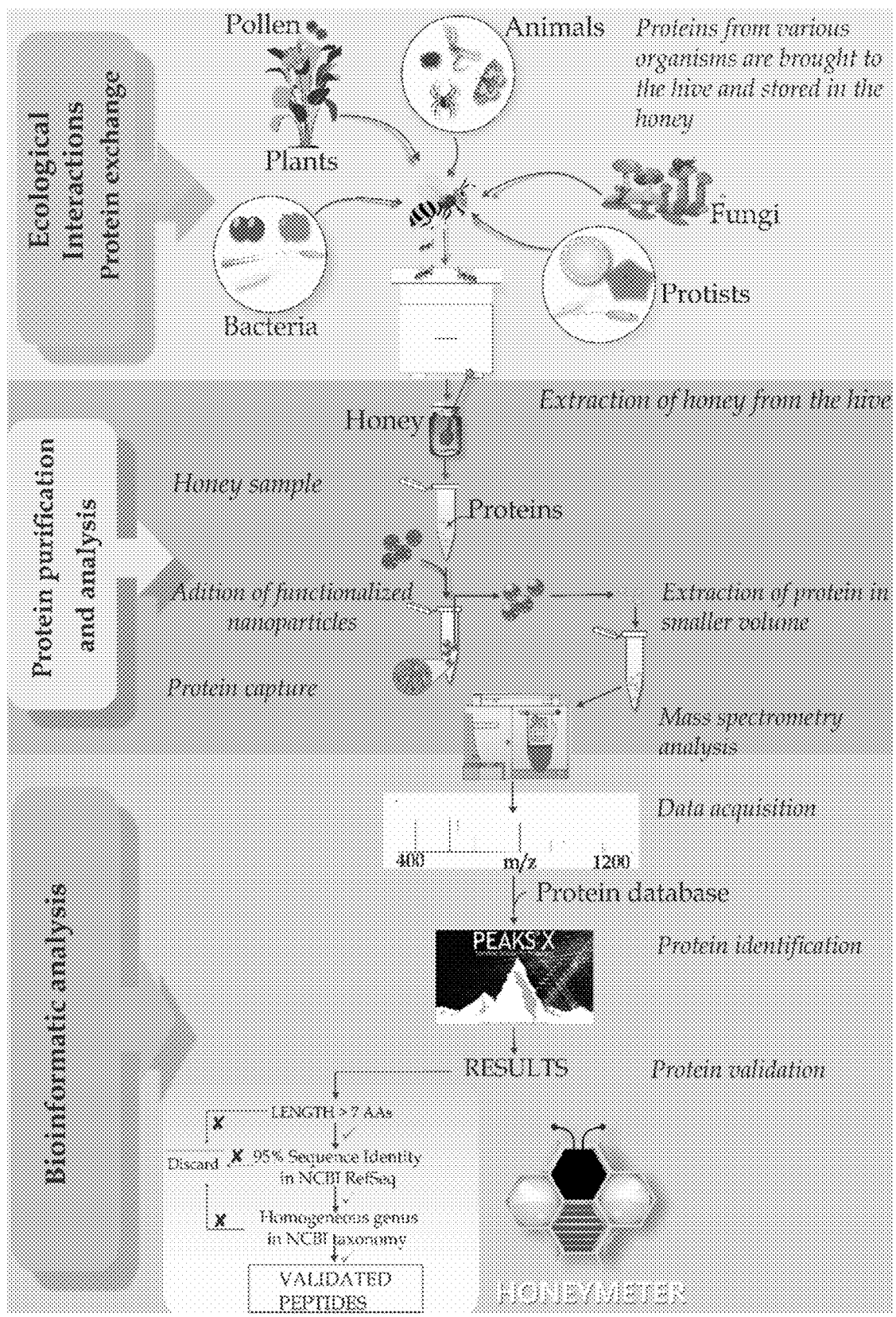
FIG. 6. Enrichment workflow is used in conjunction with mass spectrometry analysis to identify peptides in the honey. Novel bioinformatics analysis is performed for peptide authentication and organism detection.
Figure 7A:
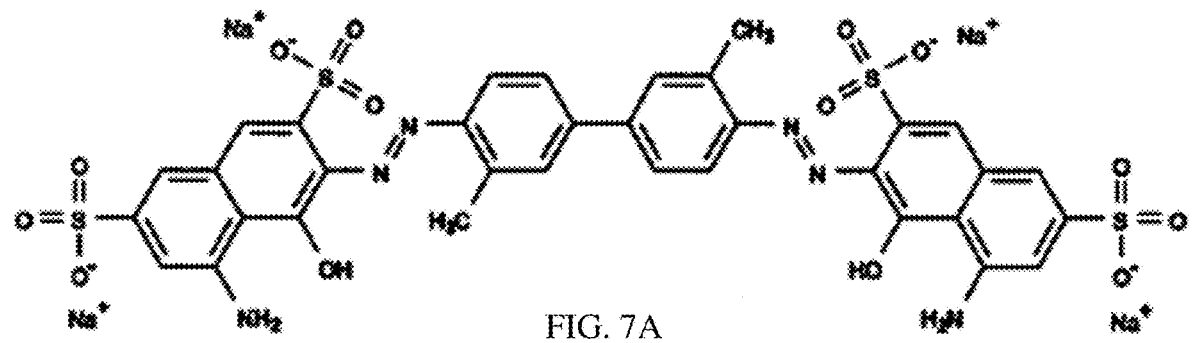
FIGS. 7A-G. Exemplary affinity dyes according to some embodiments of the disclosure include (A) trypan blue, (B) reactive blue 221, (C) bismarck brown, (D) cibacron blue, (E) alcian blue, (F) N-(4-amino-2,5-dimethoxyphenyl)benzamide, and (G) disodium 2-[(4-{ethyl[(3-sulfonatophenyl)methyl]amino}phenyl)(4-{ethyl[(3-sulfonatophenyl)methyl]iminiumyl}cyclohexa-2,5-dien-1-ylidene)methyl]-5-hydroxybenzene-1-sulfonate.
Figure 7B:
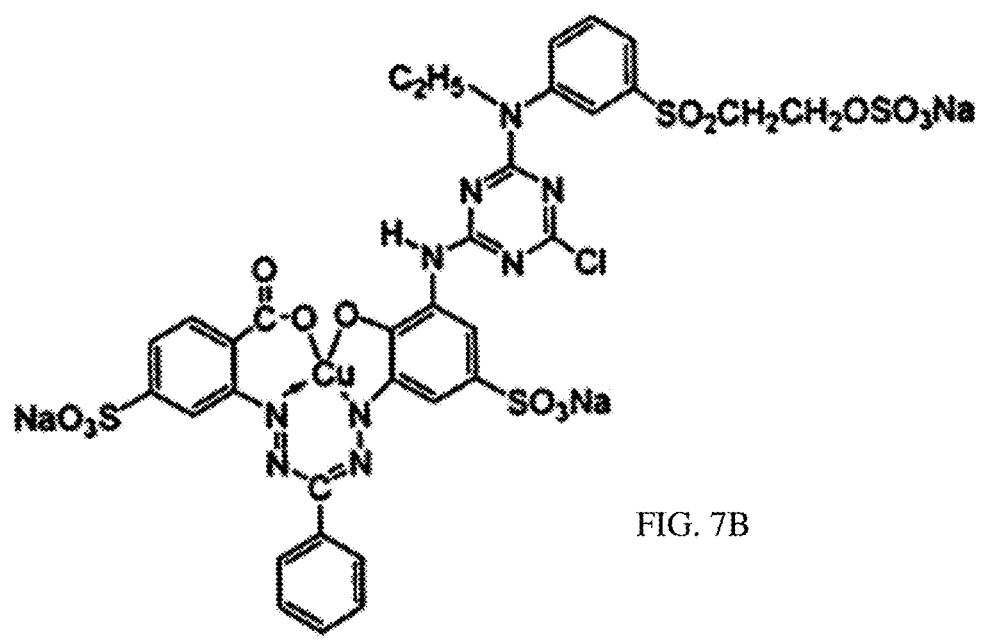
Figure 7C:
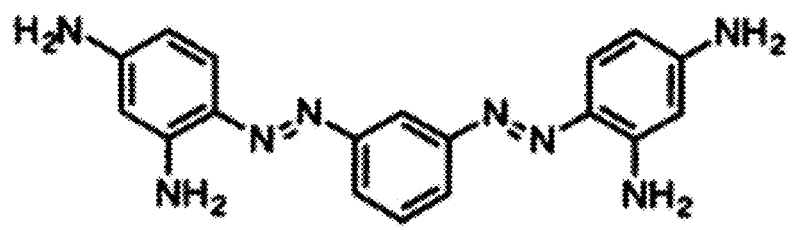
Figure 7D:
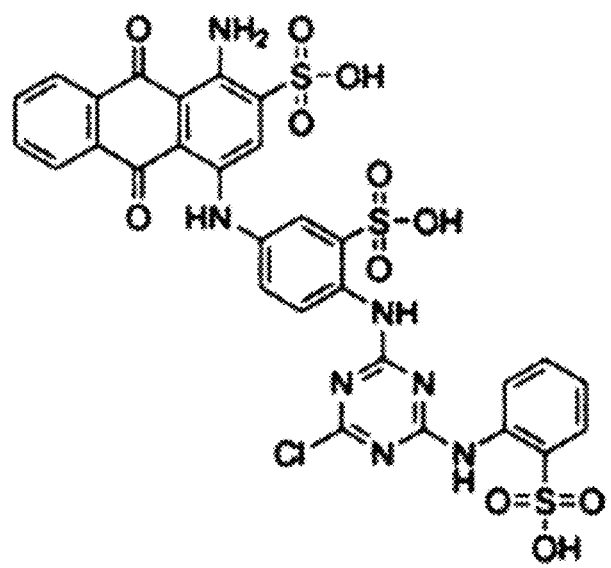
Figure 7E:
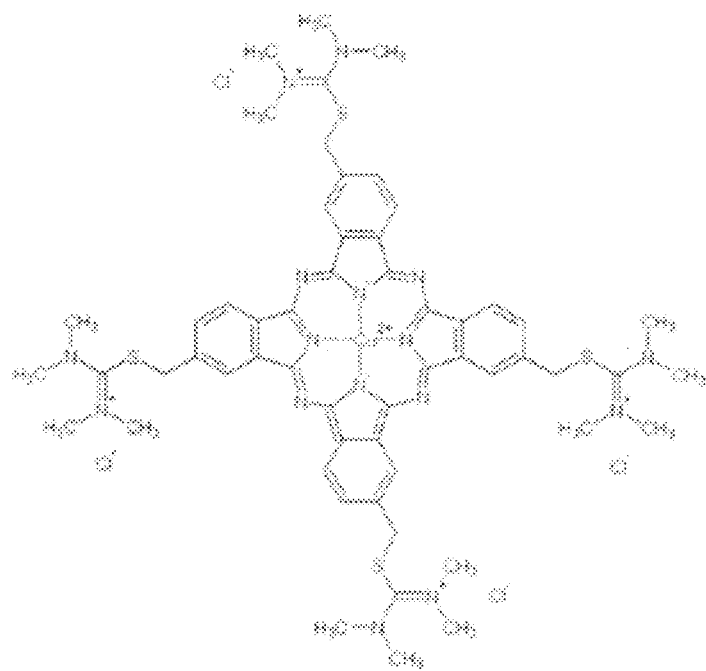
Figure 7F:
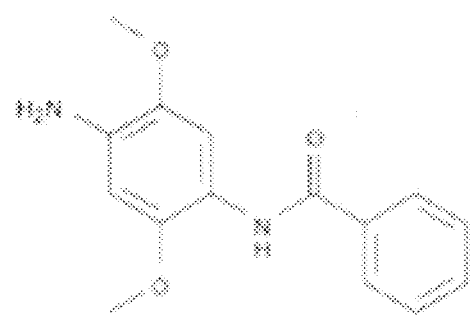
Figure 7G:
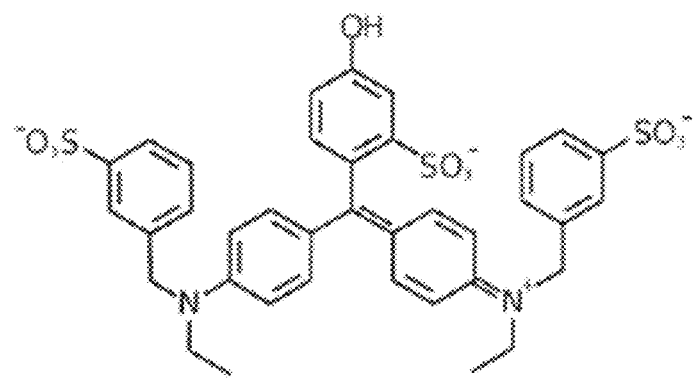

The honey samples varied significantly in total protein concentration; thus, the main output of this analysis is a variation of peptide abundance among the samples as shown in FIG. 4. In comparative studies, honey sample volumes were adjusted to have the same total protein concentration. Most of the identified peptides, like the ones shown in Table 1, are secretory proteins with a high percentage of major royal jelly proteins previously reported in other proteomics studies[4,16,32,33] showing the accuracy of this method.

the number of fungal peptides. Hymenoptaecin is a well-known antimicrobial peptide secreted in the honey to fight fungi and Gram-negative bacteria[34]. Hymenoptaecin may be used to early diagnose potential diseases since it is one of the broad-spectrum antibiotics secreted when the bee contracts a pathogen. Defensin-1 is another peptide produced by the bee when an infection is occurring. Previous studies reported the efficacy of defensin-1 against gram-positive[35], gram-negative bacteria[36], and fungi[37]. Defensin-1 activity extends for 2 weeks; therefore, its detection in the honey could indicate a prolonged infection in the colony.

Collectively, these data demonstrate that the experimental and informatics pipeline have sufficient analytical sensitivity to detect honeybee markers in the honey.

Honeybee Microbiome is Represented in Honey.

The honey gut microbiome is an integral player of honeybee health. It has been proposed that microbiome dysbiosis is linked to honeybee disease. Recent studies have shown the importance of honeybee microbiota in its metabolism and immune response against pathogens and stress condi-

TABLE 1

Example results of MS and bioinformatics analysis performed on three selected *Apis mellifra* proteins.

| Peptide sequence | Protein | Accession number | Organism | Function |
|---|---|---|---|---|
| PNDAQPYIFQEVIDYGNEAISKR<br>GTKIDNWWDNGSNQIAFSR<br>NTAYNFDYPQVPYTVK<br>ANTYNFDYPQVPYTVKNFHPR<br>EQFIDMVAR<br>YSYEISNAFE (SEQ ID NO: 1) | Alpha-amylase | AAM20738 | *Apis mellifera* | Signal peptide |
| YLHQFAPEQPDLNYYNPVVLDDMQNVLR<br>LHQFAPEQPDLNYYNPVVLDDMQNVLR<br>ILISQDAKFGNF<br>QAYYLHQFAPEQPDLNYYNPVVLDDMQ<br>NVLR<br>DVLDEFPQPK<br>FLDEPLSGETNDPNKTEYTLK<br>(SEQ ID NO: 2) | Alpha-glucosidase | PBC27950 | *Apis mellifera* | Signal peptide |
| LTLDNNQSVQVR<br>ITLDNNQSVQVR<br>SQLDDIYDYLEFNAGPLR<br>SNKEFDFVIIGGGTAGSILAR<br>VIDASIMPEVTSGNTNAPTMMIAEKGADIIKQD<br>WGVK<br>VNDVLRSNKEFDFVIIGGGTAGSILAR<br>(SEQ ID NO: 3) | Glucose dehydrogenase | XP_394209 | *Apis mellifera* | Signal peptide |

Honey samples also provided valuable information about the relationship between honey antibiotic properties and the presence of microorganisms. Antibiotic peptides, a constituent of hymenoptaecin, defensin-1, and Major Royal Jelly 1, were detected. Hymenoptaecin, in particular, was detected in 7 out of 15 of the honey samples and correlated with the presence/number of fungal peptides. Although not significant, the number of hymenoptaecin peptides trended with tions[38,39]. Disturbance of the honeybee gut population has negative effects on bee health highly noticeable during harsh winters where poor nutrition can affect honeybee gut population increasing honey mortality[40].

The present study revealed peptides from honeybee microbiome enabling organism identification in each colony. Example organisms and peptides are shown in Table 2.

TABLE 2

Example results of MS and bioinformatics analysis performed on selected honeybee microbiome peptides.

| Genus | Phylum or division | Accession number | Host | Peptide |
|---|---|---|---|---|
| Gammaproteobacteria sp. | Bacteria | OUW89226 | *Apis mellifera* | LVMELYADNVNK (SEQ ID NO: 4) |

TABLE 2-continued

Example results of MS and bioinformatics analysis performed on selected honeybee microbiome peptides.

| Genus | Phylum or division | Accession number | Host | Peptide |
|---|---|---|---|---|
| Pseudomonas sp. | Bacteria | WP_108119142 | Apis mellifera | DSAPAVVTIEGASDADGK (SEQ ID NO: 5) |
| Snodgrassella alvi | Bacteria | WP_100115220 | Apis mellifera | QLYDTNNDVSNLSSSLTTK (SEQ ID NO: 6) |
| Lactobacillus sp. | Bacteria | WP_054605660 | Apis mellifera | EGGHTVGAGVVSDIEE (SEQ ID NO: 7) |
| Microbacterium sp. | Bacteria | WP_047544473 | Apis mellifera | QMMGDTLR (SEQ ID NO: 8) |
| Bifidobacterium sp. | Bacteria | WP_110412339 | Apis mellifera | GAVESPGAVAYP (SEQ ID NO: 9) |
| Gilliamella sp. | Bacteria | WP_065632895 | Apis mellifera | DDYPDGPK (SEQ ID NO: 10) |

Previous studies have shown that the honeybee guts are colonized by nine core bacterial species clusters[38] including *Snodgrassella alvi, Gilliamella apicola, Lactobacillus* sp., *Bifidobacterium* sp., *Bartonella apis, Parasaccharibacter apium*, and *Frischella perrana*. All known microbiota species were identified in this study. Also, other opportunistic environmental bacteria were identified in honey including Gammaproteobacteria bacterium, *Klebsiella variicola*, and *Pantoea* sp. We found that the identified peptides from these species belonged to metabolic enzymes such as carbohydrate kinase, methionine tRNA ligase, alcohol dehydrogenase, and cellulose biosynthesis protein BcsC suggesting metabolically active bacteria.

In addition to the nine core bacterial species of the gut microbiome, honeybees host a variety of gram-positive and gram-negative bacteria of diverse origin that can fluctuate depending on local environmental conditions and the ecosystem. Gram-positive bacteria constitute 27% of the honeybee microbiome and are also known to exist in honey. A number of Gram-positive bacteria were found in this proteomic study. Peptides from *Clostridium, Bacillus,* and *Streptococcus* genera were detected. *Clostridium* and *Bacillus* are known to be present in the vicinity of the hive, particularly in the soil or dust and plants including flowers and pollen. These microorganisms are carried to the hive by the workers, and the larvae incorporate them through their diet. When pollen is collected and brought to the hive, it is mixed with honey and fermented to form beebread[41,42]. As a result, the organisms that were originally in the particles of pollen are integrated into the beebread that is later utilized to feed the larvae. Olaitan et al.[43] have previously identified *Clostridium* and *Bacillus* in honey and honeybee intestines, but the mechanism of colonization of the honeybee larvae intestines is not well understood and requires further exploration.

Peptides from the genus *Brevibacillus* sp. were also detected in two honey samples. Detection of these genera in the honey has great significance to understand the colony health due to the antimicrobial compounds produced by *Brevibacillus* sp.[44] Recently, *Brevibacillus laterosporus* has been isolated from *Apis mellifera* guts and has been attributed a positive effect on the colony. Its presence was correlated with increased colony member numbers and with honey production due to the antimicrobial activity of a cyclo (Leu-Pro) peptide produced by *Brevibacillus laterosporus*[45]. Further information is needed to fully understand the relationship between this genus and the honeybee, but its presence could indicate a colony more robust benefiting from the antimicrobial compounds secreted by *Brevibacillus* sp.

Gram-negative bacteria constitute 70% of the bee microbiome. In addition to the core bacteria previously described, a variety of gram-negative bacteria were identified in the honey including *Acinetobacter, Citrobacter, Enterobacter, Erwinia, Escherichia, Gluconobacter, Klebsiella,* and *Pseudomonas* (Table 3). These genera have been previously reported[29] in the honeybee gut and in the honey, and their presence was associated with different essential, digestive functions. For instance, *Gluconobacter*,[41] located in the hypopharyngeal glands, is responsible for the production of glucose oxidase, detected in the analyzed honey samples.

TABLE 3

Example results of MS and bioinformatics analysis performed on selected honeybee pathogen peptides.

| Pathogen | Accession number | Host | Peptide |
|---|---|---|---|
| Varroa destructor | XP_022658905 | Apis mellifera | VNGGGGALGGGGSGMLK (SEQ ID NO: 11) |
| Paenibacillus apiarius | WP_087435967 | Apis mellifera | FQLQDPLR (SEQ ID NO: 12) |
| Ascosphaera apis | KZZ86841 | Apis mellifera | DVMRAGSHMGLGQFR (SEQ ID NO: 13) |

TABLE 3-continued

Example results of MS and bioinformatics analysis performed on selected honeybee pathogen peptides.

| Pathogen | Accession number | Host | Peptide |
|---|---|---|---|
| Aspergillus sp. | OJI83583 | Apis mellifera | SAAGNVIDSGATTPTK (SEQ ID NO: 14) |
| Nosema ceranae | XP_024331649 | Apis mellifera | KKQDHNLR (SEQ ID NO: 15) |
| Tropilaelaps mercedesae | OQR71435 | Apis mellifera | LMNDDVFAAYR (SEQ ID NO: 16) |
| Apis mellifera filamentous virus | YP_009165850 | Apis mellifera | VTTAPLRAQASSPTQSGR (SEQ ID NO: 17) |

Monitoring honeybee microbiome is crucial to understand the colony health. As compared to other microbiome studies based on microorganism identification via DNA sequencing, this work provides a complementary set of information by revealing functionally relevant proteomic information. Peptides from honeybee microbiome in the honey could contribute to microbiome monitoring process through a less invasive method than currently used.

Pathogen Derived Peptides Signal the Presence of Disease.

One of the big obstacles in resolving the pollinator crisis is the lack of a system-based, comprehensive molecular recording of honey bees and their ecosystem that would provide signals of: a) environmental stressors and perturbation, such as disease inducing agents, b) changes in the bee symbiotic species, and c) changes in the honey bee defense response. Prompt identification of collapse etiology would inform appropriate prevention and intervention strategies.

The use of functionalized nanoparticles and bioinformatic analysis enabled the detection and identification of peptides from bee pathogens in honey from collapsing hives. This new approach allows the detection of a wide variety of pathogens in one analysis with no harm to the bees. For the first time, peptides deriving from *Varroa destructor, Paenibacillus* sp., *Ascosphaera apis, Aspergillus* sp., *Nosema ceranae, Tropilaelaps mercedesae*, and *Apis mellifera* filamentous virus were detected in honey, indicative of pathogen presence.

The presence of peptides from viruses was variable among the samples, and in some cases, absent. Most of these peptides belong to the *Apis mellifera* filamentous virus (AmFV) and were present in 10 out of the 15 analyzed samples. Samples from Argentina, H8 and H9, did not contain peptides from *Apis mellifera* filamentous virus even though AmFV has been previously reported[46] in the area.

Although some of the pathogens that affect honeybees can be easily diagnosed through simple inspection of the colony (e.g. *Varroa destructor*), others are more difficult and require experienced beekeepers (e.g. bee viruses[47]). In these cases, a proteomic analysis of a honey sample could, as shown, help with the diagnosis of micro and macroorganisms present in the hive that affect colony health, and therefore, treatment of the disease when appropriate.

Honey is a Molecular Biorepository of the Ecosystem the Honeybee Colony Interacts with.

Most of the honey samples were classified as multiflowered-honey from unknown origin. This information was confirmed by the diversity of plant peptides obtained in each sample through this proteomics analysis. Peptides deriving from more than eighty varieties of plants from the classes Viridiplantae, Liliopsida, Pinopsia, and Magnoliopsida were detected in the analyzed samples (Table 4). Particularly, hives of samples H8 and H9 were reported as located close to a sunflower field, indeed, peptides from *Helianthus annuus* were detected and identified in both samples.

TABLE 4

Example results of MS and bioinformatics analysis from plant and pollen proteins.

| Plant | Accession number | Peptide |
|---|---|---|
| Arabidopsis thaliana | NP_001190688 | WGGGMGGGGGGGGGSGGGGGRGGGPP RGGLDNVR (SEQ ID NO: 18) |
| Brassica sp. | XP_013634532 | LYFYQDTGPTPAR (SEQ ID NO: 19) |
| Cinnamomum micranthum f. kanehirae | RWR86256 | VNISNEEAVNSLR (SEQ ID NO: 20) |
| Nymphaea colorata | XP_031497610 | LLGANVNNLLK (SEQ ID NO: 21) |
| Papaver somniferum | XP_026423691 | LLEEFGYQEVGHLR (SEQ ID NO: 22) |
| Parasponia andersonii | PON55093 | LLMELYADVVPR (SEQ ID NO: 23) |
| Prunus sp. | XP_021808920 | FATTSAHDFSYMK (SEQ ID NO: 24) |
| Pyrus sp. | XP_009372014 | GVNPNNAATLPAK (SEQ ID NO: 25) |

TABLE 4-continued

Example results of MS and bioinformatics analysis from plant and pollen proteins.

| Plant | Accession number | Peptide |
|---|---|---|
| Rosa chinensis | XP_024195900 | TTGDLGDNWNSMTSR (SEQ ID NO: 26) |
| Saccharum sp. | CBZ05941 | RPSSLVGEELK (SEQ ID NO: 27) |
| Solanum sp. | XP_015057160 | ETVSGEMILNVKSK (SEQ ID NO: 28) |
| Vitis vinifera | XP_002278123 | SLASDASAAATWVR (SEQ ID NO: 29) |

Most of the identified plant peptides were derived from pollen particles collected by the bees and brought to the hive. Every year, honeybees collect between 57 kg of pollen per colony[42] to fulfill dietary needs. Pollen is the bees' main source of proteins, lipids, carbohydrates, and vitamins and contains up to 200 different substances. A previous study[48] has shown that bees use proteases such as trypsin, chymotrypsin, elastase (midgut endopeptidases), and leucine aminopeptidase (exopeptidase) to digest dietary proteins originated from pollen, nectar, and sap of plants. Bee digestion reduce the length of honey resident plant peptides. The remaining sequence of amino acids from these digested proteins are sufficiently conserved in the honey to be assigned to an organism through proteomics and bioinformatic analysis. Considering that bees can travel as far as 10 km[49], a proteomic analysis of a honey sample could provide information on the origin of the pollen collected, the plant population in the hive vicinity, and the type of honey which will be commercialized.

Pollen also contains substances that elicit allergic reactions in susceptible human individuals. Some patients develop allergic reactions to honey when they eat it. A study has shown that these patients are allergic to enzymes secreted by the bee and to pollen proteins contained in the ingested honey[50], but very little is known about the advantages of ingesting honey to prevent allergies in patients who do not develop symptoms against honey bee proteins. A recent study[51] has shown that the administration of Tualang honey in high doses to patients with allergic rhinitis improves their symptoms, and it was suggested as a complementary therapy, but data from a similar study carried out using *Apis mellifera* honey showed the opposite effect[52]. In this study, we have investigated the honey allergome by using the Structural Database of Allergenic Proteins[53] and the allergen names from the IUIS website[54]

Information from proteomics analysis could be used to identify more precisely the origin of these allergies, and the relationship between allergy and the presence of a plant-originated allergen in the honey.

Peptides from Plant Pathogens.

Environmental stressors, such as pollution and overpopulation, or diseases and pests can compromise wild plant health and crop production, the latter severely damaging agricultural economies. Prompt intervention to prevent crop disease has the potential to save the harvest and minimize losses.

A variety of peptides from plant pathogens were, for the first time, detected in the honey through proteomics and bioinformatics analysis (Table 5). Bacteria such as *Agrobacterium* sp. *Burkholderia glumae*, *Erwinia* sp., *Flavobacterium* sp., *Glaesserella parasuis*, *Helicobacter pylori*, *Mycoplasma auris*, *Pantoea* sp, *Pectobacterium* sp., *Pseudomonas syringae*, *Streptomyces* sp., and *Xanthomonas* sp. were successfully identified in the honey samples.

TABLE 5

Example results of MS and bioinformatics analysis from plant pathogens.

| Pathogen | Accession number | Peptide |
|---|---|---|
| Aureobasidium pullulans | TIA16774 | PSTSHSNVTAANDDMSEKQAIEGGPR (SEQ ID NO: 30) |
| Blumeria graminis | CCU81609 | RERDQSMR (SEQ ID NO: 31) |
| Burkholderia sp. | WP_059783841 | EPAANPDTTAR (SEQ ID NO: 32) |
| Diaporthe helianthin | POS81432 | FFTVNGPNSPR (SEQ ID NO: 33) |
| Erwinia sp. | WP_067705332 | FWQVLSPR (SEQ ID NO: 34) |
| Monilinia fructicola | KAA8575341 | NLAPKCDEVYR (SEQ ID NO: 35) |
| Monosporascus cannonballus | RYO79027 | TMYSSLNPTTNK (SEQ ID NO: 36) |
| Pantoea sp | WP_063877149 | SPSAEVAKMVEDDLGNQR (SEQ ID NO: 37) |
| Pectobacterium sp. | WP_116166552 | NAVNDLLMSQR (SEQ ID NO: 38) |

TABLE 5-continued

Example results of MS and bioinformatics analysis from plant pathogens.

| Pathogen | Accession number | Peptide |
|---|---|---|
| *Pseudomonas syringae* | WP_116865693 | SGNQIAFSR (SEQ ID NO: 39) |
| *Rhodotorula toruloides* | EGU13656 | CLFGEADEAGELDGTPDLQTR (SEQ ID NO: 40) |
| *Streptomyces* sp. | WP_156207550 | LLGADVDDLMR (SEQ ID NO: 41) |

Studies have shown that when the bees leave the hive searching for pollen, their bodies build-up positive static charge when flying[55] while flowers and their components have a negative charge[56]. This difference in charge allows honeybees to collect pollen and other components present on the surface of the flowers. Therefore, it is hypothesized that pathogenic bacteria in the pollen particles or the vicinity of the flowers are collected and taken back to the hive driven by the same phenomenon. Furthermore, the detection and identification of pathogenic plant bacteria in the honey could be key to understanding plant diseases and host-pathogen interactions.

Pathogenic organisms identified in this study are considered the top 10 most pathogenic bacteria in plants[57]. As part of the review carried out by Mansfield et. al, *Pseudomonas syringae* ranked as number 1 bacterial pathogens that affect the fruit industry worldwide[58]. Further, *Agrobacterium*, *Xanthomonas*, and *Erwinia* occupied the next places due to the impact in the agricultural sector caused by crop losses. Peptides from all the bacteria mentioned before were detected in the honey samples and unambiguously assigned to these organisms allowing their accurate identification.

Similarly, it is hypothesized that pathogenic fungi are carried by the bee and integrated into the honey through the static charge process mentioned before. Organisms from fungi taxa such as *Aureobasidium pullulans*, *Rhodotorula* sp., *Monilinia fructicola*, *Blumeria graminis*, *Diaporthe helianthin*, *Monilinia laxa*, *Penicillium brasilianum*, *Stereum hirsutum*, *Hirsutella minnesotensis*, *Monosporascus cannonballus*, *Ustilaginoidea virens* were found. Remarkably, organisms like *Aureobasidium pullulans* and *Rhodotorula* sp. have been reported as beneficial pathogens in plants. The presence of *Aureobasidium pullulans* in grapevine plant roots and vicinity reduced the number of pathogenic microorganisms and stimulate plant immune system[59]. Similarly, the members of the genus *Rhodotorula* sp. have shown remarkable potential as plant-growth enhancer[60].

Honey proteomics could provide a way of monitoring diseases, bacterial and fungal, of agriculturally relevant crops and wild plants in a radius of 10 km from the hive. As shown in this section, honey is a revolutionary information biorepository for agricultural monitoring that can be used to address many unmet needs including crop pathogens and pests, crop beneficial microorganisms, crop health and productivity metrics, and local environmental monitoring.

Conclusion

Honeybees are the main type of pollinator in ecosystems that contain flowering plants; thus, it is crucial to find a new way to identify, in early stages, environmental factors that can affect the stability of the colony and cause its collapse. We demonstrated that honey is a revolutionary information biorepository for individualized diagnosis and prevention of colony collapse, and agricultural monitoring, that can be used to address many unmet needs: 1) colony health assessments, including stress and microbiome defenses; 2) honeybee pathogens of all categories; 3) crop pathogens and pests; 4) crop health and productivity metrics; 5) local human allergens; 6) local environmental monitoring; and 7) novel medicinal compound discovery.

Example 2

Figure 8:
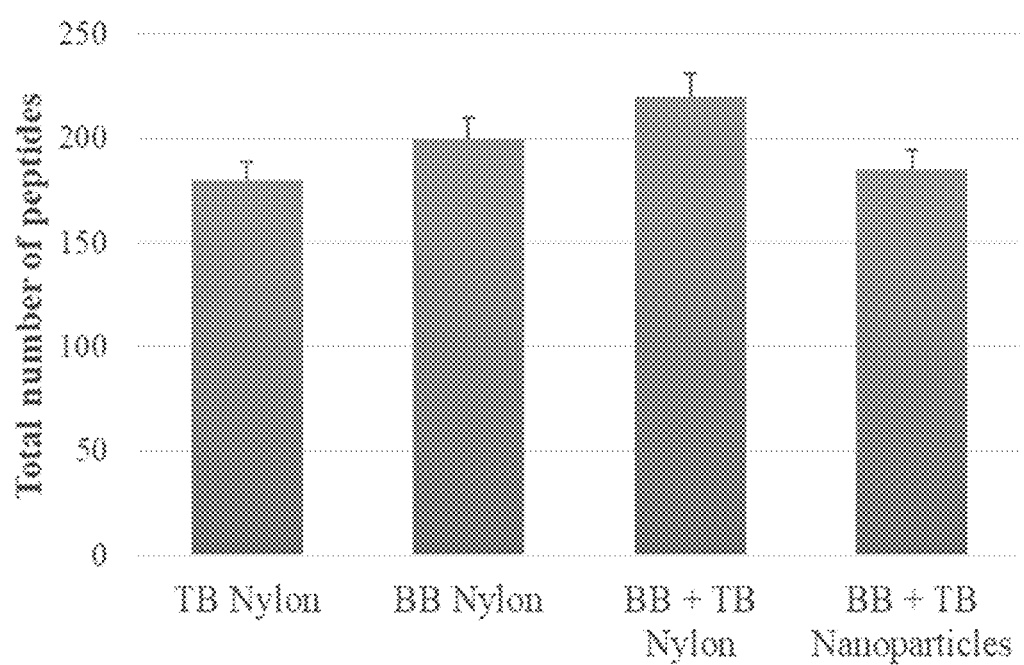
FIG. 8. Bar graph showing dye-functionalized nylon fibers and dye-functionalized nanoparticles efficiently capture *Apis mellifera* peptides in honey with similar yield.

In Example 1, affinity hydrogel nanoparticles were used; however, equivalent results can be achieved using alternative solid-state affinity materials (e.g. dye functionalized glass wool or nylon fibers). As shown in FIG. 8, dye-functionalized nylon fibers and dye-functionalized nanoparticles efficiently capture *Apis mellifera* peptides in honey with similar yield. The total number of identified *Apis mellifera* peptides is reported for different affinity capture materials: nylon fibers functionalized with Trypan Blue, nylon fibers functionalized with Bismarck Brown, nylon fibers functionalized with Trypan Blue and Bismarck Brown, and nanoparticles functionalized with Bismarck Brown and Trypan Blue; error bars represent % CV over three replicates.

Nylon staining and mass spectrometry analysis was performed as follows: 0.1 g of Bismark Brown and 0.1 g of Trypan Blue were separately dissolved in 10 mL of 5% Acetic Acid at room temperature under stirring. 5 ml of dye solution was added to 0.4 g of nylon filaments (Ø=0.5 mm, length=3 cm, Archie Bray Clay Business, #666) and let incubate at 100° C. for 1 hour. Stained nylon filaments were washed repeatedly with Milli-Q water until all the unbound dye was removed. Stained nylon filaments were then dried at 50° C. for 1 hour. 5 g of honey was diluted to 10 mL of Milli-Q water and dissolved at 40° C. for 15 min. Aliquots of 0.5 mL honey solution were incubated with: 1) 0.1 g of Trypan Blue-functionalyzed nylon; 2) 0.1 g of Bismark Brown-functionalized nylon; 3) 0.05 g of Bismark Brown-functionalized nylon and 0.05 Trypan Blue-functionalized nylon; 4) 75 μl of NIPAm/AAc/Bismarck Brown and 25 μl of NIPA/AAc/Trypan Blue for 30 min at room temperature under rotation.

Nanoparticles were centrifuged and washed 3 times with Milli-Q water. Nylon was compressed to the bottom of the vial and washed 3 times with Milli-Q water. Both the nanoparticle pellet and the dye-functionalized nylon were re-suspended in 30 μl of elution buffer solution consisting of 1% Rapigest SF (Waters) and 5% TCEP in $NH_4HCO_3$ 50 mM, and 5 μl TCEP and incubated for 20 min at room temperature. 170 μl of $NH_4HCO_3$ was added to each sample and samples were alkylated with 50 mM iodoacetamide at room temperature in the dark for 20 minutes. Enzymatic digestion was performed overnight in the presence of 2 μl (0.5 μg/μl) of sequencing grade trypsin (Promega, V5113) in 50 mM ammonium bicarbonate at 37° C. The next day 2 μl of 100% trifluoracetic acid (TFA) were added to stop digestion and samples were incubated for 30 minutes at 37° C. to degrade the Rapigest solution. Samples were then desalted and analyzed with an Orbitrap Fusion™ Tribrid™ Mass Spectrometer (Thermo Scientific, Waltham, MA) as described in Example 1. Peptide identification was performed using MaxQuant and acceptable false discovery rate (FDR) based on forward-reverse decoy <1%. Spectra were searched against a database of *Apis mellifera* obtained from uniprot.org.

REFERENCES (1) Lewkowski, O.; Mureşan, C. I.; Dobritzsch, D.; Fuszard, M.; Erler, S. The Effect of Diet on the Composition and Stability of Proteins Secreted by Honey Bees in Honey. *Insects* 2019, 10 (9).
(2) Mandal, M. D.; Mandal, S. Honey: Its Medicinal Property and Antibacterial Activity. *Asian Pacific Journal of Tropical Biomedicine* 2011, 1 (2), 154-160.
(3) De-Melo, A. A. M.; Almeida-Muradian, L. B. de; Sancho, M. T.; Pascual-Mate, A. Composition and Properties of *Apis mellifera* Honey: A Review. *Journal of Apicultural Research* 2018, 57 (1), 5-37.
(4) Erban, T.; Shcherbachenko, E.; Talacko, P.; Harant, K. The Unique Protein Composition of Honey Revealed by Comprehensive Proteomic Analysis: Allergens, Venomlike Proteins, Antibacterial Properties, Royal Jelly Proteins, Serine Proteases, and Their Inhibitors. *Journal of Natural Products* 2019, 82 (5), 1217-1226.
(5) Di Girolamo, F.; D'Amato, A.; Righetti, P. G. Assessment of the Floral Origin of Honey via Proteomic Tools. *J Proteomics* 2012, 75 (12), 3688-3693.
(6) Kim, S.; Kim, K.; Lee, J. H.; Han, S. H.; Lee, S. H. Differential Expression of Acetylcholinesterase 1 in Response to Various Stress Factors in Honey Bee Workers. *Scientific Reports* 2019, 9 (1), 10342.
(7) Johnson, R. M.; Evans, J. D.; Robinson, G. E.; Berenbaum, M. R. Changes in Transcript Abundance Relating to Colony Collapse Disorder in Honey Bees (*Apis mellifera*). *Proc. Natl. Acad. Sci. U.S.A.* 2009, 106 (35), 14790-14795.
(8) vanEngelsdorp, D.; Evans, J. D.; Saegerman, C.; Mullin, C.; Haubruge, E.; Nguyen, B. K.; Frazier, M.; Frazier, J.; Cox-Foster, D.; Chen, Y.; Underwood, R.; Tarpy, D. R.; Pettis, J. S. Colony Collapse Disorder: A Descriptive Study. *PLoS ONE* 2009, 4 (8), e6481.
(9) Colony Collapse Disorder|Protecting Bees and Other Pollinators from Pesticides|US EPA epa.gov/pollinator-protection/colony-collapse-disorder (accessed Jun. 13, 2020).
(10) Andrej Szczurek; Maciejewska, M.; Bak, B.; Wilk, J.; Wilde, J.; Siuda, M. Detecting Varroosis Using a Gas Sensor System as a Way to Face the Environmental Threat. *Science of The Total Environment* 2020, 722 (137866).
(11) Bagheri, S.; Mirzaie, M. A Mathematical Model of Honey Bee Colony Dynamics to Predict the Effect of Pollen on Colony Failure. *PLOS ONE* 2019, 14 (11), e0225632.
(12) Williams, G. R.; Tarpy, D. R.; vanEngelsdorp, D.; Chauzat, M.-P.; Cox-Foster, D. L.; Delaplane, K. S.; Neumann, P.; Pettis, J. S.; Rogers, R. E. L.; Shutler, D. Colony Collapse Disorder in Context. *Bioessays* 2010, 32 (10), 845-846.
(13) Stanimirović, Z.; Glavinić, U.; Ristanić, M.; Aleksić, N.; Jovanović, N.; Vejnović, B.; Stevanović, J. Looking for the Causes of and Solutions to the Issue of Honey Bee Colony Losses. *Acta Veterinaria* 2019, 69 (1), 1-31.
(14) Jr, J. W. W.; Rudyj, O. N. The Protein Content of Honey. *Journal of Apicultural Research* 1978, 17 (4), 234-238.
(15) Ball, D. W. The Chemical Composition of Honey. *J. Chem. Educ.* 2007, 84 (10), 1643.
(16) Zhang, Y.-Z.; Chen, Y.-F.; Wu, Y.-Q.; Si, J.-J.; Zhang, C.-P.; Zheng, H.-Q.; Hu, F.-L. Discrimination of the Entomological Origin of Honey According to the Secretions of the Bee (*Apis Cerana* or *Apis mellifera*). *Food Research International* 2019, 116, 362-369.
(17) Tamburro, D.; Fredolini, C.; Espina, V.; Douglas, T. A.; Ranganathan, A.; Ilag, L.; Zhou, W.; Russo, P.; Espina, B. H.; Muto, G.; Petricoin, E. F.; Liotta, L. A.; Luchini, A. Multifunctional Core-Shell Nanoparticles: Discovery of Previously Invisible Biomarkers. *J. Am. Chem. Soc.* 2011, 133 (47), 19178-19188.
(18) Protein Identification & Quantification Software, PTM & Variant Search. Bioinformatics Solutions Inc.
(19) Protein BLAST: search protein databases using a protein query blast.ncbi.nlm.nih.gov/Blast.cgi?PROGRAM=blastp&PAGE_TYPE=BlastSearch&LINK_LOC=blasthome (accessed Aug. 6, 2020).
(20) Mureşan, C. I.; Buttstedt, A. PH-Dependent Stability of Honey Bee (*Apis mellifera*) Major Royal Jelly Proteins. *Scientific Reports* 2019, 9 (1), 9014.
(21) Hu, H.; Bezabih, G.; Feng, M.; Wei, Q.; Zhang, X.; Wu, F.; Meng, L.; Fang, Y.; Han, B.; Ma, C.; Li, J. In-Depth Proteome of the Hypopharyngeal Glands of Honeybee Workers Reveals Highly Activated Protein and Energy Metabolism in Priming the Secretion of Royal Jelly. *Molecular & Cellular Proteomics* 2019, 18 (4), 606-621.
(22) Butler, C. G. The Choice of Drinking Water by the Honeybee. *Journal of Experimental Biology* 1940, 17 (3), 253-261.
(23) Junker, R. R.; Loewel, C.; Gross, R.; Dötterl, S.; Keller, A.; Blüthgen, N. Composition of Epiphytic Bacterial Communities Differs on Petals and Leaves. *Plant Biology* 2011, 13 (6), 918-924.
(24) Ushio, M.; Yamasaki, E.; Takasu, H.; Nagano, A. J.; Fujinaga, S.; Honjo, M. N.; Ikemoto, M.; Sakai, S.; Kudoh, H. Microbial Communities on Flower Surfaces Act as Signatures of Pollinator Visitation. *Scientific Reports* 2015, 5 (1), 8695.
(25) Evans, J.; Schwarz, R.; Childers, A. HoloBee Database V2016.1, 2016.
(26) Elsas, J. D. van; Trevors, J. T.; Rosado, A. S.; Nannipieri, P. *Modern Soil Microbiology, Third Edition*; CRC Press, 2019.
(27) Paul, E. *Soil Microbiology, Ecology and Biochemistry*; Academic Press, 2014.
(28) Cabral, J. P. S. Water Microbiology. Bacterial Pathogens and Water. International *Journal of Environmental Research and Public Health* 2010, 7 (10), 3657-3703.
(29) Silva, M. S.; Rabadzhiev, Y.; Eller, M. R.; Iliev, I.; Ivanova, I.; Santana, W. C. Microorganisms in Honey. *Honey Analysis* 2017.
(30) Snowdon, J. A.; Cliver, D. O. Microorganisms in Honey. *International Journal of Food Microbiology* 1996, 31 (1), 1-26.
(31) Weiner, C. N.; Hilpert, A.; Werner, M.; Linsenmair, K. E.; Blüthgen, N. Pollen Amino Acids and Flower Specialisation in Solitary Bees. *Apidologie* 2010, 41 (4), 476-487.
(32) Chua, L. S.; Lee, J. Y.; Chan, G. F. Honey Protein Extraction and Determination by Mass Spectrometry. *Anal Bioanal Chem* 2013, 405 (10), 3063-3074.

(33) Characterization of the Proteins in Honey: Analytical Letters: Vol 48, No 4 tandfonline.com/doi/abs/10.1080/00032719.2014.952374 (accessed Jun. 14, 2020).
(34) Li, Y.; Xiang, Q.; Zhang, Q.; Huang, Y.; Su, Z. Overview on the Recent Study of Antimicrobial Peptides: Origins, Functions, Relative Mechanisms and Application. *Peptides* 2012, 37 (2), 207-215.
(35) Danihlik, J.; Aronstein, K.; Petřivalský, M. Antimicrobial Peptides: A Key Component of Honey Bee Innate Immunity. *Journal of Apicultural Research* 2015, 54 (2), 123-136.
(36) Bulet, P.; Hetru, C.; Dimarcq, J. L.; Hoffmann, D. Antimicrobial Peptides in Insects; Structure and Function. *Dev. Comp. Immunol.* 1999, 23 (4-5), 329-344.
(37) Yamauchi, H. Two Novel Insect Defensins from Larvae of the Cupreous Chafer, *Anomala cuprea*: Purification, Amino Acid Sequences and Antibacterial Activity. *Insect Biochem. Mol. Biol.* 2001, 32 (1), 75-84.
(38) Gut microbial communities of social bees | Nature Reviews Microbiology
(39) Raymann, K.; Moran, N. A. The Role of the Gut Microbiome in Health and Disease of Adult Honey Bee Workers. *Curr Opin Insect Sci* 2018, 26, 97-104.
(40) Vojvodic, S.; Rehan, S. M.; Anderson, K. E. Microbial Gut Diversity of Africanized and European Honey Bee Larval Instars. *PLOS ONE* 2013, 8 (8), e72106.
(41) Gilliam, M. Identification and Roles of Non-Pathogenic Microflora Associated with Honey Bees1Mention of a Proprietary Product or Company Name Does Not Constitute an Endorsement of This Product by the U.S. Department of Agriculture.1. *FEMS Microbiology Letters* 1997, 155 (1), 1-10.
(42) Ellis, A.; Ellis, J. D.; O'Malley, M. K.; Nalen, C. M. Z. The Benefits of Pollen to Honey Bees. 3.
(43) Olaitan, P. B.; Adeleke, O. E.; Ola, I. O. Honey: A Reservoir for Microorganisms and an Inhibitory Agent for Microbes. *Afr Health Sci* 2007, 7 (3), 159-165.
(44) Yang, X. Brevibacillin, an Antimicrobial Lipopeptide Discovered from Genus *Brevibacillus*: Structural Elucidation, Mode of Action, Fermentation and Application in Commercial Apple Juice, The Ohio State University, 2017.
(45) Khaled, J. M.; Al-Mekhlafi, F. A.; Mothana, R. A.; Alharbi, N. S.; Alzahami, K. E.; Sharafaddin, A. H.; Kadaikunnan, S.; Alobaidi, A. S.; Bayaqoob, N. I.; Govindarajan, M.; Benelli, G. *Brevibacillus laterosporus* Isolated from the Digestive Tract of Honeybees Has High Antimicrobial Activity and Promotes Growth and Productivity of Honeybee's Colonies. *Environ Sci Pollut Res* 2018, 25 (11), 10447-10455.
(46) *Quintana*, S.; Brasesco, C.; Porrini, L. P.; Gerónimo, V. D.; Eguaras, M. J.; Maggi, M. First Molecular Detection of *Apis mellifera* Filamentous Virus (AmFV) in Honey Bees (*Apis mellifera*) in Argentina. *Journal of Apicultural Research* 2019, 0 (0), 1-4.
(47) Tantillo, G.; Bottaro, M.; Di Pinto, A.; Martella, V.; Di Pinto, P.; Terio, V. Virus Infections of Honeybees *Apis mellifera*. *Ital J Food Saf* 2015, 4 (3).
(48) Rossano, R.; Larocca, M.; Polito, T.; Perna, A. M.; Padula, M. C.; Martelli, G.; Riccio, P. What Are the Proteolytic Enzymes of Honey and What They Do Tell Us? A Fingerprint Analysis by 2-D Zymography of Unifloral Honeys. *PLoS One* 2012, 7 (11).
(49) Fun Facts americanbeejournal.com/tiposlinks/funfacts/ (accessed Jun. 14, 2020).
(50) Bauer, L.; Kohlich, A.; Hirschwehr, R.; Siemann, U.; Ebner, H.; Schemer, O.; Kraft, D.; Ebner, C. Food Allergy to Honey: Pollen or Bee Products?: Characterization of Allergenic Proteins in Honey by Means of Immunoblotting. *Journal of Allergy and Clinical Immunology* 1996, 97 (1), 65-73.
(51) Asha'ari, Z. A.; Ahmad, M. Z.; Jihan, W. S.; Che, C. M.; Leman, I. Ingestion of Honey Improves the Symptoms of Allergic Rhinitis: Evidence from a Randomized Placebo-Controlled Trial in the East Coast of Peninsular Malaysia. *Ann Saudi Med* 2013, 33 (5), 469-475.
(52) Rajan, T. V.; Tennen, H.; Lindquist, R. L.; Cohen, L.; Clive, J. Effect of Ingestion of Honey on Symptoms of Rhinoconjunctivitis. *Ann. Allergy Asthma Immunol.* 2002, 88 (2), 198-203.
(53) SDAP: Structural Database of Allergenic Proteins fermi.utmb.edu/ (accessed Aug. 18, 2020).
(54) WHO/IUIS Allergen Nomenclature Home Page allergen.org/index.php (accessed Aug. 18, 2020).
(55) Edwards, D. K. Electrostatic Charges on Insects Due to Contact with Different Substrates. *Can. J. Zool.* 1962, 40 (4), 579-584.
(56) Zakon, H. H. Electric Fields of Flowers Stimulate the Sensory Hairs of Bumble Bees. *Proc Natl Acad Sci USA* 2016, 113 (26), 7020-7021.
(57) Mansfield, J.; Genin, S.; Magori, S.; Citovsky, V.; Sriariyanum, M.; Ronald, P.; Dow, M.; Verdier, V.; Beer, S. V.; Machado, M. A.; Toth, I.; Salmond, G.; Foster, G. D. Top 10 Plant Pathogenic Bacteria in Molecular Plant Pathology. Molecular Plant Pathology 2012, 13 (6), 614-629.
(58) Vanneste, J. L. The Scientific, Economic, and Social Impacts of the New Zealand Outbreak of Bacterial Canker of Kiwifruit (*Pseudomonas syringae* Pv. Actinidiae). *Annual Review of Phytopathology* 2017, 55 (1), 377-399.
(59) Pinto, C.; Custódio, V.; Nunes, M.; Songy, A.; Rabenoelina, F.; Courteaux, B.; Clément, C.; Gomes, A. C.; Fontaine, F. Understand the Potential Role of *Aureobasidium pullulans*, a Resident Microorganism From Grapevine, to Prevent the Infection Caused by *Diplodia seriata*. *Front Microbiol* 2018, 9, 3047.
(60) Sen, D.; Paul, K.; Saha, C.; Mukherjee, G.; Nag, M.; Ghosh, S.; Das, A.; Seal, A.; Tripathy, S. A Unique Life-Strategy of an Endophytic Yeast *Rhodotorula Mucilaginosa* JGTA-S1—a Comparative Genomics Viewpoint. *DNA Research* 2019, 26 (2), 131-146.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of assessing the risk of colony collapse disorder (CCD) in a bee hive, comprising:
   contacting a honey sample obtained from the bee hive with a substrate functionalized with one or more reactive dyes;
   recovering proteins associated with the substrate;
   determining an amino acid sequence of the proteins; and
   determining that the bee hive is at an increased risk for CCD when the amino acid sequence is from a bee pathogen or a bee stress biomarker, or
   determining that the bee hive is not at an increased risk for CCD when the amino acid sequence is not from a bee pathogen or a bee stress biomarker.

2. The method of claim 1, wherein the bee pathogen is selected from the group consisting of *Varroa destructor*, *Paenibacillus* sp., *Ascosphaera apis*, *Aspergillus* sp., *Nosema ceranae*, *Tropilaelaps mercedesae*, and *Apis mellifera* filamentous virus.

3. The method of claim 1, wherein the bee stress biomarker is a heat shock protein or bee-derived antibacterial peptide.

4. The method of claim 1, further comprising treating the bee hive for CCD when it is determined that the bee hive is at an increased risk for CCD.

5. The method of claim 4, wherein treating the bee hive comprises administering an antimicrobial agent and/or isolating the bee hive from other hives.

* * * * *